United States Patent
Elands et al.

(10) Patent No.: US 12,049,500 B2
(45) Date of Patent: Jul. 30, 2024

(54) ANTI-NECTIN-4-ANTIBODIES AND USES THEREOF

(71) Applicants: EMERGENCE THERAPEUTICS GMBH, Duisburg (DE); UNIVERSITE D'AIX-MARSEILLE, Marseilles (FR); INSERM (INSTITUT NATIONAL DE LA SANTE ET DE LA RECHERCHE MEDICALE), Paris (FR); INSTITUT JEAN PAOLI & IRENE CALMETTES, Marseilles (FR); CENTRE NATIONAL DE LA RECHERCHE SCIENTIFIQUE—CNRS, Paris (FR)

(72) Inventors: Jack Elands, Forest (BE); Florence L'Hospice, Primelin (FR); Xavier Préville, Roquefort les Pins (FR); Daniel Olive, Marseilles (FR); Marc Lopez, Marseilles (FR)

(73) Assignees: EMERGENCE THERAPEUTICS GmbH, Duisburg (DE); UNIVERSITE D'AIX-MARSEILLE, Marseilles (FR); INSERM (INSTITUT NATIONAL DE LA SANTE ET DE LA RECHERCHE MEDICALE), Paris (FR); INSTITUT JEAN PAOLI & IRENE CALMETTES, Marseilles (FR); CENTRE NATIONAL DE LA RECHERCHE SCIENTIFIQUE—CNRS-, Paris (FR)

( * ) Notice: Subject to any disclaimer, the term of this patent is extended or adjusted under 35 U.S.C. 154(b) by 0 days.

(21) Appl. No.: 18/263,430

(22) PCT Filed: Mar. 31, 2022

(86) PCT No.: PCT/EP2022/058626
§ 371 (c)(1),
(2) Date: Jul. 28, 2023

(87) PCT Pub. No.: WO2022/207822
PCT Pub. Date: Oct. 6, 2022

(65) Prior Publication Data
US 2024/0034791 A1 Feb. 1, 2024

(30) Foreign Application Priority Data

| | | |
|---|---|---|
| Mar. 31, 2021 | (EP) | 21166441 |
| Apr. 28, 2021 | (EP) | 21170941 |
| May 7, 2021 | (EP) | 21172723 |
| Nov. 19, 2021 | (EP) | 21209332 |

(51) Int. Cl.
*A61P 35/00* (2006.01)
*A61K 47/68* (2017.01)
*C07K 16/28* (2006.01)

(52) U.S. Cl.
CPC .... *C07K 16/2803* (2013.01); *A61K 47/68037* (2023.08); *A61K 47/6849* (2017.08); *A61P 35/00* (2018.01); *C07K 2317/21* (2013.01); *C07K 2317/24* (2013.01); *C07K 2317/31* (2013.01)

(58) Field of Classification Search
CPC .................................................. C07K 16/2803
USPC ........................................................ 424/136.1
See application file for complete search history.

(56) References Cited

PUBLICATIONS

Wu, Sam et al: "Cutaneous toxicity associated with enfortumab vedotin treatment of metastatic urothelial carcinoma", Dermatology Online Journal, vol. 25, No. 2, Feb. 15, 2019, 4 pages, XP002804424.
Dobry, Allison S. et al: "Cutaneous reactions with enfortumab vedotin: A case series and review of the literature", JAAD Case Reports, vol. 14, Aug. 1, 2021, pp. 7-9, XP055849552.
Hirotsu, Kelsey E. et al: "Clinicopathologic characterization of enfortumab vedotin-associated cutaneous toxicity in patients with urothelial carcinoma", Journal of the American Academy of Dermatology, Dec. 1, 2020, 2 pages, XP055849554.
International Search Report issued in PCT/EP2022/058626 dated Jun. 10, 2022, 3 pgs.

*Primary Examiner* — Sean E Aeder
(74) *Attorney, Agent, or Firm* — M. Scott McBride

(57) ABSTRACT

The present invention relates to antibodies having specificity to Nectin-4 and uses thereof.

Figure 1:
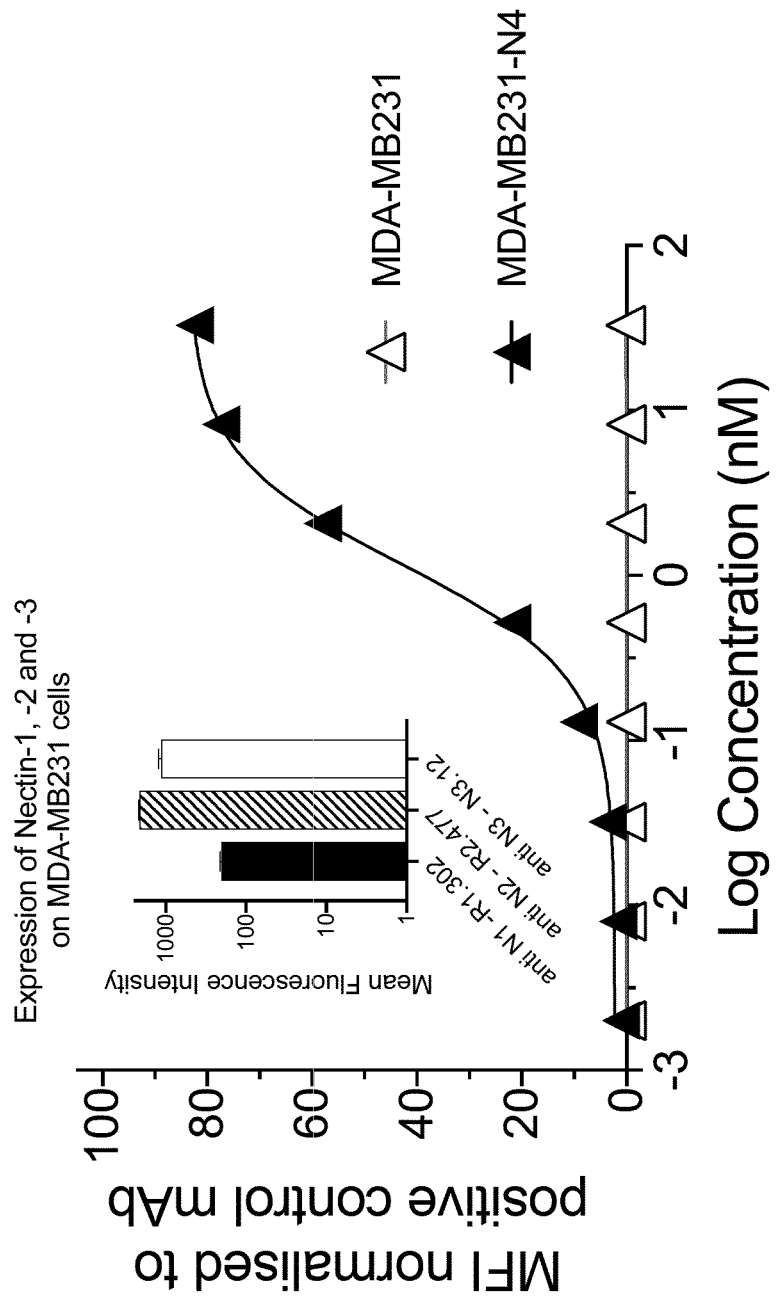

20 Claims, 26 Drawing Sheets
Specification includes a Sequence Listing.

Figure 7
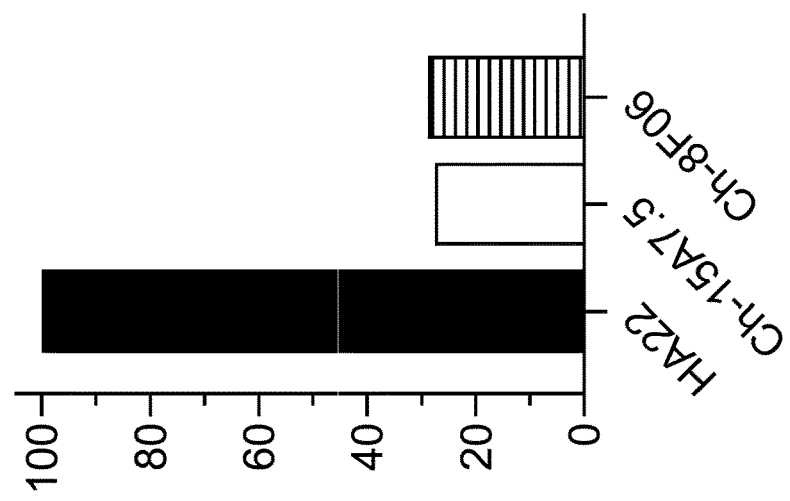
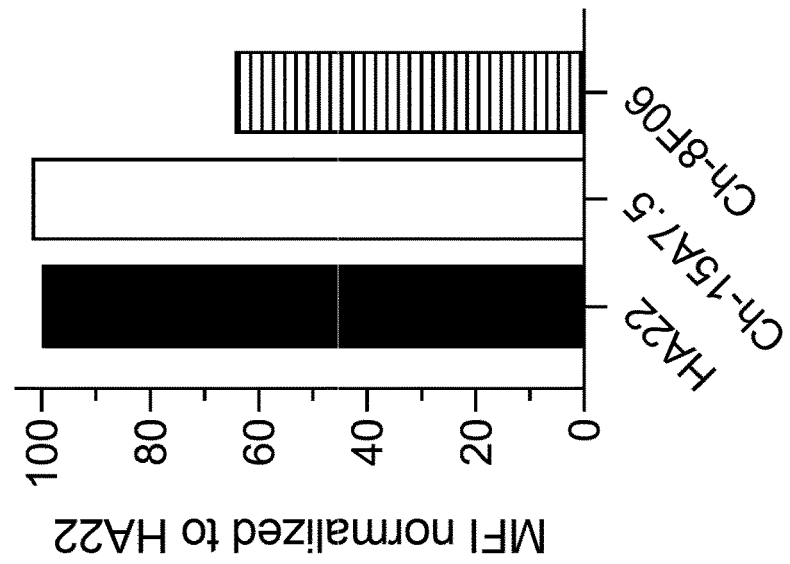

Figure 20

- Antibody clone 5A12.2

>VH_5A12.2
QIQLQQSGAELVKPGASVTLSCKTSGFTFNSMYISWLKQKPGQSLEWIAWIYAGTGGTRFN
QKFTGKVQLTVDTSSSTAYMQFSSLTDDSAIYYCAIRSGFVPMDYWGQGTSVTVSS

>VK_5A12.2
SIVMTQTPKFLLVSAGDRVTITCKASQSVSNDVAWYQQKPGQSPKLLIYYASNRYTGVPDR
FTGSGYGTDFTFTISTVQAEDLAVYFCQQDYSSPWTFGGGTKLEIK

CDR : IMGT nomenclature

Figure 21

- Antibody clone 9A2.7

>VH_9A2.7
QVQLQQPGAELVRPGASVKLSCKASGYNFTTFWINWVKQRPGQGLEWIGNIYPSDSYANYNQKFKDKATLTVDKSSTTAYMQLSSPTSEDSAVYYCTRPSYFGRNSFAYWGQGTLVTVSA

>VK_9A2.7
DIVMTQSPSSLVVSVGEKVTMSCKSSQSLLYSVNHKNYLAWYQQKPGQSPKLLIYWASTRESGVPDRFTGSGSGTDFSLTISSVKAEDLAVYYCHQYYTYPLTFGAGTKLELK

CDR : IMGT nomenclature

Figure 22

- Antibody clone 3A1.4

>VH_3A1.4
DVQLQESGPSLVKPSQTLSLTCSVTGDSITSGYWNWIRKFPGNKLEYMGYISNSGITYYNPSLKSRISITRDTSKNQYFLQLNSVTAEDTATYYCTRFGSTMILYYTMDYWGQGTSVTVSS

>VK_3A1.4
DIVMTQSPVTLSVTPGDRVSLSCRASQSISDYLHWYQQKSQESPRLLIKYASKSISGIPSRFSGSGSGSNFTLSINSVEPEDVGVYYCQNGHSFPLTFGAGTKLELK

CDR : IMGT nomenclature

Figure 23

- Antibody clone 8F06

>VH_8F06
EVQLQQSGPELVKPGASVKMSCKASGYTFTSYVMHWVKQKPGQGLEWIGYINPYNDGTK
YNEKFKGKATLTSDKSSSTAYMELSSLTSEDSAVYYCVTLFAYWGQGTLVTVSA

>VK_8F06
QIVLTQSPAIMSASPGEKVTMTCSASSSISYMHWYQQKPGTSPKRWIYDTSKLASGVPARF
SGSGSGTSYSLTISSMEAEDAATYYCHQRSSYPFTFGSGTKLEIK

CDR : IMGT nomenclature

Figure 24

- Parental antibody clone 15A7.5

>VH_15A7.5

EVKLVESGGGLVQPGGSRKLSCAASGFTFS*NYGMA*WVRQAPGKGPEWVAF*ISNLAYGI NYADTVT*GRFTISRENAKNTLYLEMRSLRSEDTAMYYCAR*GARATGWFAY*WGQGTLVT VSA

>VK_15A7.5

DIVMTQSQKFMSTSIGDRVSVTCKAS*QNVDTH*VAWYQEKPGQSPKALIY*SASYRYSGVP DRFTGSGSGTDFTLTISNVQSEDLADYFCQQ*YNSYPLT*FGGGTKLEIK

CDR : IMGT nomenclature, *Kabat nomenclature*

Figure 25

- Humanized Variants 15A7.5

> H0_15A7.5
EVQLVESGGGLVQPGGSLRLSCAA$^S$GFTF$^S$NYG$^M$MWVRQAPGKGLEWV $^F$ISNLAY( $^N$YADSVKG$^R$FTISRDNAKNSLYLQMNSLRAEDTAVYY$^C$A$^R$GARATGWFAY$^W$GQGTLVTVSS

> H1_15A7.5
EVQLVESGGGLVQPGGSLRLSCAA$^S$GFTF$^S$NYG$^M$A$^W$VRQAPGKGLEWV$^S$$^F$ISNLAYGI$^N$YADTVTG$^R$FTISRDNAKNSLYLQMNSLRAEDTAVYY$^C$A$^R$GARATGWFAY$^W$GQGTLVTVSS

>H2_15A7.5
EVQLVESGGGLVQPGGSLRLSCAA$^S$GFTF$^S$NYG$^M$A$^W$VRQAPGKGLEWV$^{AF}$ISNLAYGI$^N$YADTVTG$^R$FTISRDNAKNSLYLQMNSLRAEDTAVYY$^C$A$^R$GARATGWFAY$^W$GQGTLVTVSS

>H3_15A7.5
EVQLVESGGGLVQPGGSLRLSCAA$^S$GFTF$^S$NYG$^M$A$^W$VRQAPGKGPEWV$^{AF}$ISNLAYGI$^N$YADTVTG$^R$FTISRDNAKNSLYLQMNSLRAEDTAVYYCARGARATGWFAYWGQGTLVTVSS

> L0_15A7.5
DIQMTQSPSSLSASVGDRVTIT$^C$RA$^S$QNVDTH$^V$AWFQQKPGKAPKSLI$^Y$SAS$^Y$LQSGVPSRFSGSGSGTDFTLTISSLQPEDFATYY$^C$QQYNSYPLT$^F$GGGTKVEIK

>L1_15A7.5
DIQMTQSPSSLSASVGDRVTITC$^C$KA$^S$QNVDTH$^V$A$^W$FQQKPGKAPKSLI$^Y$SAS$^Y$RYS$^G$VPSRFSGSGSGTDFTLTISSLQPEDFATYY$^C$QQYNSYPLT$^F$GGGTKVEIK

> L2_15A7.5
DIQMTQSPSSLSASVGDRVTIT$^C$KA$^S$QNVDTH$^V$A$^W$YQQKPGKAPKALI$^Y$SAS$^Y$RYS$^G$VPSRFSGSGSGTDFTLTISSLQPEDFATYY$^C$QQYNSYPLT$^F$GGGTKVEIK

> L3_15A7.5
DIQMTQSPSSLSASVGDRVTIT$^C$KA$^S$QNVDTH$^V$A$^W$YYQQKPGKSPKALI$^Y$SAS$^Y$RYS$^G$VPSRFSGSGSGTDFTLTISSLQPEDFATYY$^C$QQYNSYPLT$^F$GGGTKVEIK

CDR : IMGT nomenclature / *Kabat nomenclature* / anchor IMGT and/or Kabat / back-mutations

Figure 26

Humanized 15A7.5 variants

| Clone/variant | KD (nM) | Ka (1/Ms) | Kdis (1/s) | $R^2$ |
|---|---|---|---|---|
| Ch-15A7.5 | 45.9 | $7.52^E+04$ | $3.45^E-03$ | 0.98 |
| 15A7.5_H1L2 | 52 | $8.01^E+04$ | $4.16^E-03$ | 0.97 |
| 15A7.5_H1L3 | 50 | $8.24^E+04$ | $4.12^E-03$ | 0.97 |
| 15A7.5_H2L2 | 59.7 | $7.79^E+04$ | $4.65^E-03$ | 0.97 |
| 15A7.5_H2L3 | 60 | $8.00^E+04$ | $4.80^E-03$ | 0.97 |
| 15A7.5_H3L2 | 55.5 | $8.81^E+04$ | $4.89^E-03$ | 0.97 |
| 15A7.5_H3L3 | 58.1 | $7.86^E+04$ | $4.57^E-03$ | 0.97 |
| 15A7.5_H0L3 | Irrelevant | Irrelevant | Irrelevant | 0.92 |

SEQUENCE LISTING

<160> NUMBER OF SEQ ID NOS: 103

<210> SEQ ID NO 1
<211> LENGTH: 8
<212> TYPE: PRT
<213> ORGANISM: artificial sequence
<220> FEATURE:
<223> OTHER INFORMATION: CDR1 VH_15A7.5 IMGT

<400> SEQUENCE: 1

Gly Phe Thr Phe Ser Asn Tyr Gly
1               5

<210> SEQ ID NO 2
<211> LENGTH: 8
<212> TYPE: PRT
<213> ORGANISM: artificial sequence
<220> FEATURE:
<223> OTHER INFORMATION: CDR2 VH_15A7.5 IMGT

<400> SEQUENCE: 2

Ile Ser Asn Leu Ala Tyr Gly Ile
1               5

<210> SEQ ID NO 3
<211> LENGTH: 12
<212> TYPE: PRT
<213> ORGANISM: artificial sequence
<220> FEATURE:
<223> OTHER INFORMATION: CDR3 VH_15A7.5 IMGT

<400> SEQUENCE: 3

Ala Arg Gly Ala Arg Ala Thr Gly Trp Phe Ala Tyr
1               5                   10

<210> SEQ ID NO 4
<211> LENGTH: 6
<212> TYPE: PRT
<213> ORGANISM: artificial sequence
<220> FEATURE:
<223> OTHER INFORMATION: CDR1 VK_15A7.5 IMGT

<400> SEQUENCE: 4

Gln Asn Val Asp Thr His
1               5

<210> SEQ ID NO 5
<211> LENGTH: 3
<212> TYPE: PRT
<213> ORGANISM: artificial sequence
<220> FEATURE:
<223> OTHER INFORMATION: CDR2 VK_15A7.5 IMGT

<400> SEQUENCE: 5

Ser Ala Ser
1

<210> SEQ ID NO 6
<211> LENGTH: 9
<212> TYPE: PRT
<213> ORGANISM: artificial sequence
<220> FEATURE:
<223> OTHER INFORMATION: CDR3 VK_15A7.5 IMGT

<400> SEQUENCE: 6

Gln Gln Tyr Asn Ser Tyr Pro Leu Thr
1               5

```
<210> SEQ ID NO 7
<211> LENGTH: 5
<212> TYPE: PRT
<213> ORGANISM: artificial sequence
<220> FEATURE:
<223> OTHER INFORMATION: CDR1 VH_15A7.5 Kabat

<400> SEQUENCE: 7

Asn Tyr Gly Met Ala
1               5

<210> SEQ ID NO 8
<211> LENGTH: 17
<212> TYPE: PRT
<213> ORGANISM: artificial sequence
<220> FEATURE:
<223> OTHER INFORMATION: CDR2 VH_15A7.5 Kabat

<400> SEQUENCE: 8

Phe Ile Ser Asn Leu Ala Tyr Gly Ile Asn Tyr Ala Asp Thr Val Thr
1               5                   10                  15

Gly

<210> SEQ ID NO 9
<211> LENGTH: 10
<212> TYPE: PRT
<213> ORGANISM: artificial sequence
<220> FEATURE:
<223> OTHER INFORMATION: CDR3 VH_15A7.5 Kabat

<400> SEQUENCE: 9

Gly Ala Arg Ala Thr Gly Trp Phe Ala Tyr
1               5                   10

<210> SEQ ID NO 10
<211> LENGTH: 11
<212> TYPE: PRT
<213> ORGANISM: artificial sequence
<220> FEATURE:
<223> OTHER INFORMATION: CDR1 VK_15A7.5 Kabat

<400> SEQUENCE: 10

Lys Ala Ser Gln Asn Val Asp Thr His Val Ala
1               5                   10

<210> SEQ ID NO 11
<211> LENGTH: 7
<212> TYPE: PRT
<213> ORGANISM: artificial sequence
<220> FEATURE:
<223> OTHER INFORMATION: CDR2 VK_15A7.5 Kabat

<400> SEQUENCE: 11

Ser Ala Ser Tyr Arg Tyr Ser
1               5

<210> SEQ ID NO 12
<211> LENGTH: 9
<212> TYPE: PRT
<213> ORGANISM: artificial sequence
<220> FEATURE:
<223> OTHER INFORMATION: CDR3 VK_15A7.5 Kabat

<400> SEQUENCE: 12

Gln Gln Tyr Asn Ser Tyr Pro Leu Thr
```

<210> SEQ ID NO 13
<211> LENGTH: 119
<212> TYPE: PRT
<213> ORGANISM: artificial sequence
<220> FEATURE:
<223> OTHER INFORMATION: VH_15A7.5

<400> SEQUENCE: 13

Glu Val Lys Leu Val Glu Ser Gly Gly Gly Leu Val Gln Pro Gly Gly
1               5                   10                  15

Ser Arg Lys Leu Ser Cys Ala Ala Ser Gly Phe Thr Phe Ser Asn Tyr
            20                  25                  30

Gly Met Ala Trp Val Arg Gln Ala Pro Gly Lys Gly Pro Glu Trp Val
        35                  40                  45

Ala Phe Ile Ser Asn Leu Ala Tyr Gly Ile Asn Tyr Ala Asp Thr Val
    50                  55                  60

Thr Gly Arg Phe Thr Ile Ser Arg Glu Asn Ala Lys Asn Thr Leu Tyr
65                  70                  75                  80

Leu Glu Met Arg Ser Leu Arg Ser Glu Asp Thr Ala Met Tyr Tyr Cys
                85                  90                  95

Ala Arg Gly Ala Arg Ala Thr Gly Trp Phe Ala Tyr Trp Gly Gln Gly
            100                 105                 110

Thr Leu Val Thr Val Ser Ala
        115

<210> SEQ ID NO 14
<211> LENGTH: 107
<212> TYPE: PRT
<213> ORGANISM: artificial sequence
<220> FEATURE:
<223> OTHER INFORMATION: VK_15A7.5

<400> SEQUENCE: 14

Asp Ile Val Met Thr Gln Ser Gln Lys Phe Met Ser Thr Ser Ile Gly
1               5                   10                  15

Asp Arg Val Ser Val Thr Cys Lys Ala Ser Gln Asn Val Asp Thr His
            20                  25                  30

Val Ala Trp Tyr Gln Glu Lys Pro Gly Gln Ser Pro Lys Ala Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Gln Gln Tyr Asn Ser Tyr Pro Leu
                85                  90                  95

Thr Phe Gly Gly Gly Thr Lys Leu Glu Ile Lys
            100                 105

<210> SEQ ID NO 15
<211> LENGTH: 9
<212> TYPE: PRT
<213> ORGANISM: artificial sequence
<220> FEATURE:
<223> OTHER INFORMATION: CDR1 H0_15A7.5 IMGT

<400> SEQUENCE: 15

Gly Phe Thr Phe Ser Asn Tyr Gly Met
1               5

```
<210> SEQ ID NO 16
<211> LENGTH: 8
<212> TYPE: PRT
<213> ORGANISM: artificial sequence
<220> FEATURE:
<223> OTHER INFORMATION: CDR2 H0_15A7.5  IMGT

<400> SEQUENCE: 16

Ile Ser Asn Leu Ala Tyr Gly Ile
1               5

<210> SEQ ID NO 17
<211> LENGTH: 12
<212> TYPE: PRT
<213> ORGANISM: artificial sequence
<220> FEATURE:
<223> OTHER INFORMATION: CDR3 H0_15A7.5  IMGT

<400> SEQUENCE: 17

Ala Arg Gly Ala Arg Ala Thr Gly Trp Phe Ala Tyr
1               5                   10

<210> SEQ ID NO 18
<211> LENGTH: 6
<212> TYPE: PRT
<213> ORGANISM: artificial sequence
<220> FEATURE:
<223> OTHER INFORMATION: CDR1 L0_15A7.5 IMGT

<400> SEQUENCE: 18

Gln Asn Val Asp Thr His
1               5

<210> SEQ ID NO 19
<211> LENGTH: 3
<212> TYPE: PRT
<213> ORGANISM: artificial sequence
<220> FEATURE:
<223> OTHER INFORMATION: CDR2 L0_15A7.5 IMGT

<400> SEQUENCE: 19

Ser Ala Ser
1

<210> SEQ ID NO 20
<211> LENGTH: 9
<212> TYPE: PRT
<213> ORGANISM: artificial sequence
<220> FEATURE:
<223> OTHER INFORMATION: CDR3 L0_15A7.5 IMGT

<400> SEQUENCE: 20

Gln Gln Tyr Asn Ser Tyr Pro Leu Thr
1               5

<210> SEQ ID NO 21
<211> LENGTH: 5
<212> TYPE: PRT
<213> ORGANISM: artificial sequence
<220> FEATURE:
<223> OTHER INFORMATION: CDR1 H0_15A7.5  Kabat

<400> SEQUENCE: 21

Asn Tyr Gly Met Asn
1               5
```

```
<210> SEQ ID NO 22
<211> LENGTH: 17
<212> TYPE: PRT
<213> ORGANISM: artificial sequence
<220> FEATURE:
<223> OTHER INFORMATION: CDR2 H0_15A7.5 Kabat

<400> SEQUENCE: 22

Phe Ile Ser Asn Leu Ala Tyr Gly Ile Asn Tyr Ala Asp Ser Val Lys
1               5                   10                  15
Gly

<210> SEQ ID NO 23
<211> LENGTH: 10
<212> TYPE: PRT
<213> ORGANISM: artificial sequence
<220> FEATURE:
<223> OTHER INFORMATION: CDR3 H0_15A7.5 Kabat

<400> SEQUENCE: 23

Gly Ala Arg Ala Thr Gly Trp Phe Ala Tyr
1               5                   10

<210> SEQ ID NO 24
<211> LENGTH: 11
<212> TYPE: PRT
<213> ORGANISM: artificial sequence
<220> FEATURE:
<223> OTHER INFORMATION: CDR1 L0_15A7.5 Kabat

<400> SEQUENCE: 24

Arg Ala Ser Gln Asn Val Asp Thr His Val Ala
1               5                   10

<210> SEQ ID NO 25
<211> LENGTH: 7
<212> TYPE: PRT
<213> ORGANISM: artificial sequence
<220> FEATURE:
<223> OTHER INFORMATION: CDR2 L0_15A7.5 Kabat

<400> SEQUENCE: 25

Ser Ala Ser Tyr Leu Gln Ser
1               5

<210> SEQ ID NO 26
<211> LENGTH: 9
<212> TYPE: PRT
<213> ORGANISM: artificial sequence
<220> FEATURE:
<223> OTHER INFORMATION: CDR3 L0_15A7.5 Kabat

<400> SEQUENCE: 26

Gln Gln Tyr Asn Ser Tyr Pro Leu Thr
1               5

<210> SEQ ID NO 27
<211> LENGTH: 119
<212> TYPE: PRT
<213> ORGANISM: artificial sequence
<220> FEATURE:
<223> OTHER INFORMATION: H0_15A7.5

<400> SEQUENCE: 27

Glu Val Gln Leu Val Glu Ser Gly Gly Gly Leu Val Gln Pro Gly Gly
1               5                   10                  15
```

Ser Leu Arg Leu Ser Cys Ala Ala Ser Gly Phe Thr Phe Ser Asn Tyr
            20                  25                  30

Gly Met Asn Trp Val Arg Gln Ala Pro Gly Lys Gly Leu Glu Trp Val
        35                  40                  45

Ser Phe Ile Ser Asn Leu Ala Tyr Gly Ile Asn Tyr Ala Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Ala Arg Ala Thr Gly Trp Phe Ala Tyr Trp Gly Gln Gly
            100                 105                 110

Thr Leu Val Thr Val Ser Ser
            115

<210> SEQ ID NO 28
<211> LENGTH: 107
<212> TYPE: PRT
<213> ORGANISM: artificial sequence
<220> FEATURE:
<223> OTHER INFORMATION: L0_15A7.5

<400> SEQUENCE: 28

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asn Val Asp Thr His
            20                  25                  30

Val Ala Trp Phe Gln Gln Lys Pro Gly Lys Ala Pro Lys Ser Leu Ile
        35                  40                  45

Tyr Ser Ala Ser Tyr Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Leu
                85                  90                  95

Thr Phe Gly Gly Gly Thr Lys Val Glu Ile Lys
            100                 105

<210> SEQ ID NO 29
<211> LENGTH: 8
<212> TYPE: PRT
<213> ORGANISM: artificial sequence
<220> FEATURE:
<223> OTHER INFORMATION: CDR1 H1_15A7.5 IMGT

<400> SEQUENCE: 29

Gly Phe Thr Phe Ser Asn Tyr Gly
1               5

<210> SEQ ID NO 30
<211> LENGTH: 8
<212> TYPE: PRT
<213> ORGANISM: artificial sequence
<220> FEATURE:
<223> OTHER INFORMATION: CDR2 H1_15A7.5 IMGT

<400> SEQUENCE: 30

Ile Ser Asn Leu Ala Tyr Gly Ile
1               5

```
<210> SEQ ID NO 31
<211> LENGTH: 12
<212> TYPE: PRT
<213> ORGANISM: artificial sequence
<220> FEATURE:
<223> OTHER INFORMATION: CDR3 H1_15A7.5 IMGT

<400> SEQUENCE: 31

Ala Arg Gly Ala Arg Ala Thr Gly Trp Phe Ala Tyr
1               5                   10

<210> SEQ ID NO 32
<211> LENGTH: 6
<212> TYPE: PRT
<213> ORGANISM: artificial sequence
<220> FEATURE:
<223> OTHER INFORMATION: CDR1 L1_15A7.5 IMGT

<400> SEQUENCE: 32

Gln Asn Val Asp Thr His
1               5

<210> SEQ ID NO 33
<211> LENGTH: 3
<212> TYPE: PRT
<213> ORGANISM: artificial sequence
<220> FEATURE:
<223> OTHER INFORMATION: CDR2 L1_15A7.5 IMGT

<400> SEQUENCE: 33

Ser Ala Ser
1

<210> SEQ ID NO 34
<211> LENGTH: 9
<212> TYPE: PRT
<213> ORGANISM: artificial sequence
<220> FEATURE:
<223> OTHER INFORMATION: CDR3 L1_15A7.5 IMGT

<400> SEQUENCE: 34

Gln Gln Tyr Asn Ser Tyr Pro Leu Thr
1               5

<210> SEQ ID NO 35
<211> LENGTH: 5
<212> TYPE: PRT
<213> ORGANISM: artificial sequence
<220> FEATURE:
<223> OTHER INFORMATION: CDR1 H1_15A7.5 Kabat

<400> SEQUENCE: 35

Asn Tyr Gly Met Ala
1               5

<210> SEQ ID NO 36
<211> LENGTH: 17
<212> TYPE: PRT
<213> ORGANISM: artificial sequence
<220> FEATURE:
<223> OTHER INFORMATION: CDR2 H1_15A7.5 Kabat

<400> SEQUENCE: 36

Phe Ile Ser Asn Leu Ala Tyr Gly Ile Asn Tyr Ala Asp Thr Val Thr
1               5                   10                  15

Gly
```

<210> SEQ ID NO 37
<211> LENGTH: 10
<212> TYPE: PRT
<213> ORGANISM: artificial sequence
<220> FEATURE:
<223> OTHER INFORMATION: CDR3 H1_15A7.5 Kabat

<400> SEQUENCE: 37

Gly Ala Arg Ala Thr Gly Trp Phe Ala Tyr
1               5                   10

<210> SEQ ID NO 38
<211> LENGTH: 11
<212> TYPE: PRT
<213> ORGANISM: artificial sequence
<220> FEATURE:
<223> OTHER INFORMATION: CDR1 L1_15A7.5 Kabat

<400> SEQUENCE: 38

Lys Ala Ser Gln Asn Val Asp Thr His Val Ala
1               5                   10

<210> SEQ ID NO 39
<211> LENGTH: 7
<212> TYPE: PRT
<213> ORGANISM: artificial sequence
<220> FEATURE:
<223> OTHER INFORMATION: CDR2 L1_15A7.5 Kabat

<400> SEQUENCE: 39

Ser Ala Ser Tyr Arg Tyr Ser
1               5

<210> SEQ ID NO 40
<211> LENGTH: 9
<212> TYPE: PRT
<213> ORGANISM: artificial sequence
<220> FEATURE:
<223> OTHER INFORMATION: CDR3 L1_15A7.5 Kabat

<400> SEQUENCE: 40

Gln Gln Tyr Asn Ser Tyr Pro Leu Thr
1               5

<210> SEQ ID NO 41
<211> LENGTH: 119
<212> TYPE: PRT
<213> ORGANISM: artificial sequence
<220> FEATURE:
<223> OTHER INFORMATION: H1_15A7.5

<400> SEQUENCE: 41

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met Ala Trp Val Arg Gln Ala Pro Gly Lys Gly Leu Glu Trp Val
        35                  40                  45

Ser Phe Ile Ser Asn Leu Ala Tyr Gly Ile Asn Tyr Ala Asp Thr Val
    50                  55                  60

Thr Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys

```
                   85                  90                  95

Ala Arg Gly Ala Arg Ala Thr Gly Trp Phe Ala Tyr Trp Gly Gln Gly
               100                 105                 110

Thr Leu Val Thr Val Ser Ser
               115

<210> SEQ ID NO 42
<211> LENGTH: 108
<212> TYPE: PRT
<213> ORGANISM: artificial sequence
<220> FEATURE:
<223> OTHER INFORMATION: L1_15A7.5

<400> SEQUENCE: 42

Asp Ile Gln Met Thr Gln Ser Pro Ser Ser Leu Ser Ala Ser Val Gly
1               5                  10                  15

Asp Arg Val Thr Ile Thr Cys Cys Lys Ala Ser Gln Asn Val Asp Thr
                20                  25                  30

His Val Ala Trp Phe Gln Lys Pro Gly Lys Ala Pro Lys Ser Leu
            35                  40                  45

Ile Tyr Ser Ala Ser Tyr Arg Tyr Ser Gly Val Pro Ser Arg Phe Ser
50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Gln Tyr Asn Ser Tyr Pro
                85                  90                  95

Leu Thr Phe Gly Gly Gly Thr Lys Val Glu Ile Lys
            100                 105

<210> SEQ ID NO 43
<211> LENGTH: 8
<212> TYPE: PRT
<213> ORGANISM: artificial sequence
<220> FEATURE:
<223> OTHER INFORMATION: CDR1 H2_15A7.5 IMGT

<400> SEQUENCE: 43

Gly Phe Thr Phe Ser Asn Tyr Gly
1               5

<210> SEQ ID NO 44
<211> LENGTH: 8
<212> TYPE: PRT
<213> ORGANISM: artificial sequence
<220> FEATURE:
<223> OTHER INFORMATION: CDR2 H2_15A7.5 IMGT

<400> SEQUENCE: 44

Ile Ser Asn Leu Ala Tyr Gly Ile
1               5

<210> SEQ ID NO 45
<211> LENGTH: 12
<212> TYPE: PRT
<213> ORGANISM: artificial sequence
<220> FEATURE:
<223> OTHER INFORMATION: CDR3 H2_15A7.5 IMGT

<400> SEQUENCE: 45

Ala Arg Gly Ala Arg Ala Thr Gly Trp Phe Ala Tyr
1               5                  10
```

```
<210> SEQ ID NO 46
<211> LENGTH: 6
<212> TYPE: PRT
<213> ORGANISM: artificial sequence
<220> FEATURE:
<223> OTHER INFORMATION: CDR1 L2_15A7.5 IMGT

<400> SEQUENCE: 46

Gln Asn Val Asp Thr His
1               5

<210> SEQ ID NO 47
<211> LENGTH: 3
<212> TYPE: PRT
<213> ORGANISM: artificial sequence
<220> FEATURE:
<223> OTHER INFORMATION: CDR2 L2_15A7.5 IMGT

<400> SEQUENCE: 47

Ser Ala Ser
1

<210> SEQ ID NO 48
<211> LENGTH: 9
<212> TYPE: PRT
<213> ORGANISM: artificial sequence
<220> FEATURE:
<223> OTHER INFORMATION: CDR3 L2_15A7.5 IMGT

<400> SEQUENCE: 48

Gln Gln Tyr Asn Ser Tyr Pro Leu Thr
1               5

<210> SEQ ID NO 49
<211> LENGTH: 5
<212> TYPE: PRT
<213> ORGANISM: artificial sequence
<220> FEATURE:
<223> OTHER INFORMATION: CDR1 H2_15A7.5 Kabat

<400> SEQUENCE: 49

Asn Tyr Gly Met Ala
1               5

<210> SEQ ID NO 50
<211> LENGTH: 17
<212> TYPE: PRT
<213> ORGANISM: artificial sequence
<220> FEATURE:
<223> OTHER INFORMATION: CDR2 H2_15A7.5 Kabat

<400> SEQUENCE: 50

Phe Ile Ser Asn Leu Ala Tyr Gly Ile Asn Tyr Ala Asp Thr Val Thr
1               5                   10                  15

Gly

<210> SEQ ID NO 51
<211> LENGTH: 10
<212> TYPE: PRT
<213> ORGANISM: artificial sequence
<220> FEATURE:
<223> OTHER INFORMATION: CDR3 H2_15A7.5 Kabat

<400> SEQUENCE: 51

Gly Ala Arg Ala Thr Gly Trp Phe Ala Tyr
1               5                   10
```

<210> SEQ ID NO 52
<211> LENGTH: 11
<212> TYPE: PRT
<213> ORGANISM: artificial sequence
<220> FEATURE:
<223> OTHER INFORMATION: CDR1 L2_15A7.5 Kabat

<400> SEQUENCE: 52

Lys Ala Ser Gln Asn Val Asp Thr His Val Ala
1               5                   10

<210> SEQ ID NO 53
<211> LENGTH: 7
<212> TYPE: PRT
<213> ORGANISM: artificial sequence
<220> FEATURE:
<223> OTHER INFORMATION: CDR2 L2_15A7.5 Kabat

<400> SEQUENCE: 53

Ser Ala Ser Tyr Arg Tyr Ser
1               5

<210> SEQ ID NO 54
<211> LENGTH: 9
<212> TYPE: PRT
<213> ORGANISM: artificial sequence
<220> FEATURE:
<223> OTHER INFORMATION: CDR3 L2_15A7.5 Kabat

<400> SEQUENCE: 54

Gln Gln Tyr Asn Ser Tyr Pro Leu Thr
1               5

<210> SEQ ID NO 55
<211> LENGTH: 119
<212> TYPE: PRT
<213> ORGANISM: artificial sequence
<220> FEATURE:
<223> OTHER INFORMATION: H2_15A7.5

<400> SEQUENCE: 55

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met Ala Trp Val Arg Gln Ala Pro Gly Lys Gly Leu Glu Trp Val
        35                  40                  45

Ala Phe Ile Ser Asn Leu Ala Tyr Gly Ile Asn Tyr Ala Asp Thr Val
    50                  55                  60

Thr Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Ala Arg Ala Thr Gly Trp Phe Ala Tyr Trp Gly Gln Gly
            100                 105                 110

Thr Leu Val Thr Val Ser Ser
        115

<210> SEQ ID NO 56
<211> LENGTH: 107
<212> TYPE: PRT
<213> ORGANISM: artificial sequence
<220> FEATURE:

<223> OTHER INFORMATION: L2_15A7.5

<400> SEQUENCE: 56

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Asp Thr His
            20                  25                  30

Val Ala Trp Tyr Gln Gln Lys Pro Gly Lys Ala Pro Lys Ala Leu Ile
        35                  40                  45

Tyr Ser Ala Ser Tyr Arg Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Leu
                85                  90                  95

Thr Phe Gly Gly Gly Thr Lys Val Glu Ile Lys
            100                 105

<210> SEQ ID NO 57
<211> LENGTH: 8
<212> TYPE: PRT
<213> ORGANISM: artificial sequence
<220> FEATURE:
<223> OTHER INFORMATION: CDR1 H3_15A7.5 IMGT

<400> SEQUENCE: 57

Gly Phe Thr Phe Ser Asn Tyr Gly
1               5

<210> SEQ ID NO 58
<211> LENGTH: 8
<212> TYPE: PRT
<213> ORGANISM: artificial sequence
<220> FEATURE:
<223> OTHER INFORMATION: CDR2 H3_15A7.5 IMGT

<400> SEQUENCE: 58

Ile Ser Asn Leu Ala Tyr Gly Ile
1               5

<210> SEQ ID NO 59
<211> LENGTH: 12
<212> TYPE: PRT
<213> ORGANISM: artificial sequence
<220> FEATURE:
<223> OTHER INFORMATION: CDR3 H3_15A7.5 IMGT

<400> SEQUENCE: 59

Ala Arg Gly Ala Arg Ala Thr Gly Trp Phe Ala Tyr
1               5                   10

<210> SEQ ID NO 60
<211> LENGTH: 6
<212> TYPE: PRT
<213> ORGANISM: artificial sequence
<220> FEATURE:
<223> OTHER INFORMATION: CDR1 L3_15A7.5 IMGT

<400> SEQUENCE: 60

Gln Asn Val Asp Thr His
1               5

<210> SEQ ID NO 61

```
<211> LENGTH: 3
<212> TYPE: PRT
<213> ORGANISM: artificial sequence
<220> FEATURE:
<223> OTHER INFORMATION: CDR2 L3_15A7.5 IMGT

<400> SEQUENCE: 61

Ser Ala Ser
1

<210> SEQ ID NO 62
<211> LENGTH: 9
<212> TYPE: PRT
<213> ORGANISM: artificial sequence
<220> FEATURE:
<223> OTHER INFORMATION: CDR3 L3_15A7.5 IMGT

<400> SEQUENCE: 62

Gln Gln Tyr Asn Ser Tyr Pro Leu Thr
1               5

<210> SEQ ID NO 63
<211> LENGTH: 5
<212> TYPE: PRT
<213> ORGANISM: artificial sequence
<220> FEATURE:
<223> OTHER INFORMATION: CDR1 H3_15A7.5 Kabat

<400> SEQUENCE: 63

Asn Tyr Gly Met Ala
1               5

<210> SEQ ID NO 64
<211> LENGTH: 17
<212> TYPE: PRT
<213> ORGANISM: artificial sequence
<220> FEATURE:
<223> OTHER INFORMATION: CDR2 H3_15A7.5 Kabat

<400> SEQUENCE: 64

Phe Ile Ser Asn Leu Ala Tyr Gly Ile Asn Tyr Ala Asp Thr Val Thr
1               5                   10                  15

Gly

<210> SEQ ID NO 65
<211> LENGTH: 10
<212> TYPE: PRT
<213> ORGANISM: artificial sequence
<220> FEATURE:
<223> OTHER INFORMATION: CDR3 H3_15A7.5 Kabat

<400> SEQUENCE: 65

Gly Ala Arg Ala Thr Gly Trp Phe Ala Tyr
1               5                   10

<210> SEQ ID NO 66
<211> LENGTH: 11
<212> TYPE: PRT
<213> ORGANISM: artificial sequence
<220> FEATURE:
<223> OTHER INFORMATION: CDR1 L3_15A7.5 Kabat

<400> SEQUENCE: 66

Lys Ala Ser Gln Asn Val Asp Thr His Val Ala
1               5                   10
```

```
<210> SEQ ID NO 67
<211> LENGTH: 7
<212> TYPE: PRT
<213> ORGANISM: artificial sequence
<220> FEATURE:
<223> OTHER INFORMATION: CDR2 L3_15A7.5 Kabat

<400> SEQUENCE: 67

Ser Ala Ser Tyr Arg Tyr Ser
1               5

<210> SEQ ID NO 68
<211> LENGTH: 9
<212> TYPE: PRT
<213> ORGANISM: artificial sequence
<220> FEATURE:
<223> OTHER INFORMATION: CDR3 L3_15A7.5 Kabat

<400> SEQUENCE: 68

Gln Gln Tyr Asn Ser Tyr Pro Leu Thr
1               5

<210> SEQ ID NO 69
<211> LENGTH: 119
<212> TYPE: PRT
<213> ORGANISM: artificial sequence
<220> FEATURE:
<223> OTHER INFORMATION: H3_15A7.5

<400> SEQUENCE: 69

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met Ala Trp Val Arg Gln Ala Pro Gly Lys Gly Pro Glu Trp Val
        35                  40                  45

Ala Phe Ile Ser Asn Leu Ala Tyr Gly Ile Asn Tyr Ala Asp Thr Val
    50                  55                  60

Thr Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Ala Arg Ala Thr Gly Trp Phe Ala Tyr Trp Gly Gln Gly
            100                 105                 110

Thr Leu Val Thr Val Ser Ser
        115

<210> SEQ ID NO 70
<211> LENGTH: 108
<212> TYPE: PRT
<213> ORGANISM: artificial sequence
<220> FEATURE:
<223> OTHER INFORMATION: L3_15A7.5

<400> SEQUENCE: 70

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Asp Thr His
            20                  25                  30

Val Ala Trp Tyr Tyr Gln Gln Lys Pro Gly Lys Ser Pro Lys Ala Leu
        35                  40                  45

Ile Tyr Ser Ala Ser Tyr Arg Tyr Ser Gly Val Pro Ser Arg Phe Ser
```

```
                  50                  55                  60
Gly Ser Gly Ser Gly Thr Asp Phe Thr Leu Thr Ile Ser Ser Leu Gln
 65                  70                  75                  80

Pro Glu Asp Phe Ala Thr Tyr Tyr Cys Gln Gln Tyr Asn Ser Tyr Pro
                 85                  90                  95

Leu Thr Phe Gly Gly Gly Thr Lys Val Glu Ile Lys
            100                 105
```

<210> SEQ ID NO 71
<211> LENGTH: 8
<212> TYPE: PRT
<213> ORGANISM: artificial sequence
<220> FEATURE:
<223> OTHER INFORMATION: CDR1 VH_5A12.2

<400> SEQUENCE: 71

```
Gly Phe Thr Phe Asn Ser Met Tyr
 1               5
```

<210> SEQ ID NO 72
<211> LENGTH: 8
<212> TYPE: PRT
<213> ORGANISM: artificial sequence
<220> FEATURE:
<223> OTHER INFORMATION: CDR2 VH_5A12.2

<400> SEQUENCE: 72

```
Ile Tyr Ala Gly Thr Gly Gly Thr
 1               5
```

<210> SEQ ID NO 73
<211> LENGTH: 13
<212> TYPE: PRT
<213> ORGANISM: artificial sequence
<220> FEATURE:
<223> OTHER INFORMATION: CDR3 VH_5A12.2

<400> SEQUENCE: 73

```
Ala Ile Arg Ser Gly Phe Val Pro Met Asp Tyr Trp Gly
 1               5                  10
```

<210> SEQ ID NO 74
<211> LENGTH: 118
<212> TYPE: PRT
<213> ORGANISM: artificial sequence
<220> FEATURE:
<223> OTHER INFORMATION: VH_5A12.2

<400> SEQUENCE: 74

```
Gln Ile Gln Leu Gln Gln Ser Gly Ala Glu Leu Val Lys Pro Gly Ala
 1               5                  10                  15

Ser Val Thr Leu Ser Cys Lys Thr Ser Gly Phe Thr Phe Asn Ser Met
                20                  25                  30

Tyr Ile Ser Trp Leu Lys Gln Lys Pro Gly Gln Ser Leu Glu Trp Ile
            35                  40                  45

Ala Trp Ile Tyr Ala Gly Thr Gly Gly Thr Arg Phe Asn Gln Lys Phe
     50                  55                  60

Thr Gly Lys Val Gln Leu Thr Val Asp Thr Ser Ser Thr Ala Tyr
 65                  70                  75                  80

Met Gln Phe Ser Ser Leu Thr Thr Asp Asp Ser Ala Ile Tyr Tyr Cys
                 85                  90                  95

Ala Ile Arg Ser Gly Phe Val Pro Met Asp Tyr Trp Gly Gln Gly Thr
```

Ser Val Thr Val Ser Ser
        115

<210> SEQ ID NO 75
<211> LENGTH: 6
<212> TYPE: PRT
<213> ORGANISM: artificial sequence
<220> FEATURE:
<223> OTHER INFORMATION: CDR1 VK_5A12.2

<400> SEQUENCE: 75

Gln Ser Val Ser Asn Asp
1               5

<210> SEQ ID NO 76
<211> LENGTH: 3
<212> TYPE: PRT
<213> ORGANISM: artificial sequence
<220> FEATURE:
<223> OTHER INFORMATION: CDR2 VK_5A12.2

<400> SEQUENCE: 76

Tyr Ala Ser
1

<210> SEQ ID NO 77
<211> LENGTH: 6
<212> TYPE: PRT
<213> ORGANISM: artificial sequence
<220> FEATURE:
<223> OTHER INFORMATION: CDR3 VK_5A12.2

<400> SEQUENCE: 77

Gln Gln Asp Tyr Ser Ser
1               5

<210> SEQ ID NO 78
<211> LENGTH: 107
<212> TYPE: PRT
<213> ORGANISM: artificial sequence
<220> FEATURE:
<223> OTHER INFORMATION: VK_5A12.2

<400> SEQUENCE: 78

Ser Ile Val Met Thr Gln Thr Pro Lys Phe Leu Leu Val Ser Ala Gly
1               5                   10                  15

Asp Arg Val Thr Ile Thr Cys Lys Ala Ser Gln Ser Val Ser Asn Asp
            20                  25                  30

Val Ala Trp Tyr Gln Gln Lys Pro Gly Gln Ser Pro Lys Leu Leu Ile
        35                  40                  45

Tyr Tyr Ala Ser Asn Arg Tyr Thr Gly Val Pro Asp Arg Phe Thr Gly
    50                  55                  60

Ser Gly Tyr Gly Thr Asp Phe Thr Phe Thr Ile Ser Thr Val Gln Ala
65                  70                  75                  80

Glu Asp Leu Ala Val Tyr Phe Cys Gln Gln Asp Tyr Ser Ser Pro Trp
                85                  90                  95

Thr Phe Gly Gly Gly Thr Lys Leu Glu Ile Lys
            100                 105

<210> SEQ ID NO 79
<211> LENGTH: 8
<212> TYPE: PRT

-continued

<213> ORGANISM: artificial sequence
<220> FEATURE:
<223> OTHER INFORMATION: CDR1 VH_9A2.7

<400> SEQUENCE: 79

Gly Tyr Asn Phe Thr Thr Phe Trp
1               5

<210> SEQ ID NO 80
<211> LENGTH: 8
<212> TYPE: PRT
<213> ORGANISM: artificial sequence
<220> FEATURE:
<223> OTHER INFORMATION: CDR2 VH_9A2.7

<400> SEQUENCE: 80

Ile Tyr Pro Ser Asp Ser Tyr Ala
1               5

<210> SEQ ID NO 81
<211> LENGTH: 13
<212> TYPE: PRT
<213> ORGANISM: artificial sequence
<220> FEATURE:
<223> OTHER INFORMATION: CDR3 VH_9A2.7

<400> SEQUENCE: 81

Thr Arg Pro Ser Tyr Phe Gly Arg Asn Ser Phe Ala Tyr
1               5                   10

<210> SEQ ID NO 82
<211> LENGTH: 120
<212> TYPE: PRT
<213> ORGANISM: artificial sequence
<220> FEATURE:
<223> OTHER INFORMATION: VH_9A2.7

<400> SEQUENCE: 82

Gln Val Gln Leu Gln Gln Pro Gly Ala Glu Leu Val Arg Pro Gly Ala
1               5                   10                  15

Ser Val Lys Leu Ser Cys Lys Ala Ser Gly Tyr Asn Phe Thr Thr Phe
            20                  25                  30

Trp Ile Asn Trp Val Lys Gln Arg Pro Gly Gln Gly Leu Glu Trp Ile
        35                  40                  45

Gly Asn Ile Tyr Pro Ser Asp Ser Tyr Ala Asn Tyr Asn Gln Lys Phe
    50                  55                  60

Lys Asp Lys Ala Thr Leu Thr Val Asp Lys Ser Ser Thr Thr Ala Tyr
65                  70                  75                  80

Met Gln Leu Ser Ser Pro Thr Ser Glu Asp Ser Ala Val Tyr Tyr Cys
                85                  90                  95

Thr Arg Pro Ser Tyr Phe Gly Arg Asn Ser Phe Ala Tyr Trp Gly Gln
            100                 105                 110

Gly Thr Leu Val Thr Val Ser Ala
        115                 120

<210> SEQ ID NO 83
<211> LENGTH: 12
<212> TYPE: PRT
<213> ORGANISM: artificial sequence
<220> FEATURE:
<223> OTHER INFORMATION: CDR1 VK_9A2.7

<400> SEQUENCE: 83

```
Gln Ser Leu Leu Tyr Ser Val Asn His Lys Asn Tyr
1               5                   10
```

<210> SEQ ID NO 84
<211> LENGTH: 3
<212> TYPE: PRT
<213> ORGANISM: artificial sequence
<220> FEATURE:
<223> OTHER INFORMATION: CDR2 VK_9A2.7

<400> SEQUENCE: 84

```
Trp Ala Ser
1
```

<210> SEQ ID NO 85
<211> LENGTH: 9
<212> TYPE: PRT
<213> ORGANISM: artificial sequence
<220> FEATURE:
<223> OTHER INFORMATION: CDR3 VK_9A2.7

<400> SEQUENCE: 85

```
His Gln Tyr Tyr Thr Tyr Pro Leu Thr
1               5
```

<210> SEQ ID NO 86
<211> LENGTH: 113
<212> TYPE: PRT
<213> ORGANISM: artificial sequence
<220> FEATURE:
<223> OTHER INFORMATION: VK_9A2.7

<400> SEQUENCE: 86

```
Asp Ile Val Met Thr Gln Ser Pro Ser Ser Leu Val Val Ser Val Gly
1               5                   10                  15

Glu Lys Val Thr Met Ser Cys Lys Ser Ser Gln Ser Leu Leu Tyr Ser
            20                  25                  30

Val Asn His Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Ser Leu Thr
65                  70                  75                  80

Ile Ser Ser Val Lys Ala Glu Asp Leu Ala Val Tyr Tyr Cys His Gln
                85                  90                  95

Tyr Tyr Thr Tyr Pro Leu Thr Phe Gly Ala Gly Thr Lys Leu Glu Leu
            100                 105                 110

Lys
```

<210> SEQ ID NO 87
<211> LENGTH: 8
<212> TYPE: PRT
<213> ORGANISM: artificial sequence
<220> FEATURE:
<223> OTHER INFORMATION: CDR1 VH_3A1.4

<400> SEQUENCE: 87

```
Gly Asp Ser Ile Thr Ser Gly Tyr
1               5
```

<210> SEQ ID NO 88
<211> LENGTH: 7
<212> TYPE: PRT

```
<213> ORGANISM: artificial sequence
<220> FEATURE:
<223> OTHER INFORMATION: CDR2 VH_3A1.4

<400> SEQUENCE: 88

Ile Ser Asn Ser Gly Ile Thr
1               5

<210> SEQ ID NO 89
<211> LENGTH: 15
<212> TYPE: PRT
<213> ORGANISM: artificial sequence
<220> FEATURE:
<223> OTHER INFORMATION: CDR3 VH_3A1.4

<400> SEQUENCE: 89

Thr Arg Phe Gly Ser Thr Met Ile Leu Tyr Tyr Thr Met Asp Tyr
1               5                   10                  15

<210> SEQ ID NO 90
<211> LENGTH: 121
<212> TYPE: PRT
<213> ORGANISM: artificial sequence
<220> FEATURE:
<223> OTHER INFORMATION: VH_3A1.4

<400> SEQUENCE: 90

Asp Val Gln Leu Gln Glu Ser Gly Pro Ser Leu Val Lys Pro Ser Gln
1               5                   10                  15

Thr Leu Ser Leu Thr Cys Ser Val Thr Gly Asp Ser Ile Thr Ser Gly
                20                  25                  30

Tyr Trp Asn Trp Ile Arg Lys Phe Pro Gly Asn Lys Leu Glu Tyr Met
            35                  40                  45

Gly Tyr Ile Ser Asn Ser Gly Ile Thr Tyr Tyr Asn Pro Ser Leu Lys
        50                  55                  60

Ser Arg Ile Ser Ile Thr Arg Asp Thr Ser Lys Asn Gln Tyr Phe Leu
65                  70                  75                  80

Gln Leu Asn Ser Val Thr Ala Glu Asp Thr Ala Thr Tyr Tyr Cys Thr
                85                  90                  95

Arg Phe Gly Ser Thr Met Ile Leu Tyr Tyr Thr Met Asp Tyr Trp Gly
            100                 105                 110

Gln Gly Thr Ser Val Thr Val Ser Ser
        115                 120

<210> SEQ ID NO 91
<211> LENGTH: 6
<212> TYPE: PRT
<213> ORGANISM: artificial sequence
<220> FEATURE:
<223> OTHER INFORMATION: CDR1 VK_3A1.4

<400> SEQUENCE: 91

Gln Ser Ile Ser Asp Tyr
1               5

<210> SEQ ID NO 92
<211> LENGTH: 3
<212> TYPE: PRT
<213> ORGANISM: artificial sequence
<220> FEATURE:
<223> OTHER INFORMATION: CDR2 VK_3A1.4

<400> SEQUENCE: 92
```

Tyr Ala Ser
1

<210> SEQ ID NO 93
<211> LENGTH: 9
<212> TYPE: PRT
<213> ORGANISM: artificial sequence
<220> FEATURE:
<223> OTHER INFORMATION: CDR3 VK_3A1.4

<400> SEQUENCE: 93

Gln Asn Gly His Ser Phe Pro Leu Thr
1               5

<210> SEQ ID NO 94
<211> LENGTH: 107
<212> TYPE: PRT
<213> ORGANISM: artificial sequence
<220> FEATURE:
<223> OTHER INFORMATION: VK_3A1.4

<400> SEQUENCE: 94

Asp Ile Val Met Thr Gln Ser Pro Val Thr Leu Ser Val Thr Pro Gly
1               5                   10                  15

Asp Arg Val Ser Leu Ser Cys Arg Ala Ser Gln Ser Ile Ser Asp Tyr
            20                  25                  30

Leu His Trp Tyr Gln Gln Lys Ser Gln Glu Ser Pro Arg Leu Leu Ile
        35                  40                  45

Lys Tyr Ala Ser Lys Ser Ile Ser Gly Ile Pro Ser Arg Phe Ser Gly
    50                  55                  60

Ser Gly Ser Gly Ser Asn Phe Thr Leu Ser Ile Asn Ser Val Glu Pro
65                  70                  75                  80

Glu Asp Val Gly Val Tyr Tyr Cys Gln Asn Gly His Ser Phe Pro Leu
                85                  90                  95

Thr Phe Gly Ala Gly Thr Lys Leu Glu Leu Lys
            100                 105

<210> SEQ ID NO 95
<211> LENGTH: 8
<212> TYPE: PRT
<213> ORGANISM: artificial sequence
<220> FEATURE:
<223> OTHER INFORMATION: CDR1 VH_8F06

<400> SEQUENCE: 95

Gly Tyr Thr Phe Thr Ser Tyr Val
1               5

<210> SEQ ID NO 96
<211> LENGTH: 8
<212> TYPE: PRT
<213> ORGANISM: artificial sequence
<220> FEATURE:
<223> OTHER INFORMATION: CDR2 VH_8F06

<400> SEQUENCE: 96

Ile Asn Pro Tyr Asn Asp Gly Thr
1               5

<210> SEQ ID NO 97
<211> LENGTH: 6
<212> TYPE: PRT
<213> ORGANISM: artificial sequence
<220> FEATURE:

<223> OTHER INFORMATION: CDR3 VH_8F06

<400> SEQUENCE: 97

Val Thr Leu Phe Ala Tyr
1               5

<210> SEQ ID NO 98
<211> LENGTH: 113
<212> TYPE: PRT
<213> ORGANISM: artificial sequence
<220> FEATURE:
<223> OTHER INFORMATION: VH_8F06

<400> SEQUENCE: 98

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Val Met His Trp Val Lys Gln Lys Pro Gly Gln Gly Leu Glu Trp Ile
        35                  40                  45

Gly Tyr Ile Asn Pro Tyr Asn Asp Gly Thr Lys Tyr Asn Glu Lys Phe
    50                  55                  60

Lys Gly Lys Ala Thr Leu Thr Ser Asp Lys Ser Ser Thr Ala Tyr
65                  70                  75                  80

Met Glu Leu Ser Ser Leu Thr Ser Glu Asp Ser Ala Val Tyr Tyr Cys
            85                  90                  95

Val Thr Leu Phe Ala Tyr Trp Gly Gln Gly Thr Leu Val Thr Val Ser
            100                 105                 110

Ala

<210> SEQ ID NO 99
<211> LENGTH: 5
<212> TYPE: PRT
<213> ORGANISM: artificial sequence
<220> FEATURE:
<223> OTHER INFORMATION: CDR1 VK_8F06

<400> SEQUENCE: 99

Ser Ser Ile Ser Tyr
1               5

<210> SEQ ID NO 100
<211> LENGTH: 3
<212> TYPE: PRT
<213> ORGANISM: artificial sequence
<220> FEATURE:
<223> OTHER INFORMATION: CDR2 VK_8F06

<400> SEQUENCE: 100

Asp Thr Ser
1

<210> SEQ ID NO 101
<211> LENGTH: 9
<212> TYPE: PRT
<213> ORGANISM: artificial sequence
<220> FEATURE:
<223> OTHER INFORMATION: CDR3 VK_8F06

<400> SEQUENCE: 101

His Gln Arg Ser Ser Tyr Pro Phe Thr
1               5

```
<210> SEQ ID NO 102
<211> LENGTH: 106
<212> TYPE: PRT
<213> ORGANISM: artificial sequence
<220> FEATURE:
<223> OTHER INFORMATION: VK_8F06

<400> SEQUENCE: 102

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ile Ser Tyr Met
            20                  25                  30

His Trp Tyr Gln Gln Lys Pro Gly Thr Ser Pro Lys Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys His Gln Arg Ser Ser Tyr Pro Phe Thr
                85                  90                  95

Phe Gly Ser Gly Thr Lys Leu Glu Ile Lys
            100                 105

<210> SEQ ID NO 103
<211> LENGTH: 107
<212> TYPE: PRT
<213> ORGANISM: artificial sequence
<220> FEATURE:
<223> OTHER INFORMATION: L3_15A7.5_mod

<400> SEQUENCE: 103

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Asp Thr His
            20                  25                  30

Val Ala Trp Tyr Gln Gln Lys Pro Gly Lys Ser Pro Lys Ala Leu
        35                  40                  45

Ile Tyr Ser Ala Ser Tyr Arg Tyr Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Cys Gln Gln Tyr Asn Ser Tyr Pro Leu
                85                  90                  95

Thr Phe Gly Gly Gly Thr Lys Val Glu Ile Lys
            100                 105
```

ANTI-NECTIN-4-ANTIBODIES AND USES THEREOF

CROSS REFERENCE TO RELATED APPLICATION

This application is a 35 U.S.C. 371 National Phase Entry Application from PCT/EP2022/058626 filed Mar. 31, 2022, which claims priority to and the benefit of European Patent Application Nos. 21166441.2 filed Mar. 31, 2021, 21170941.5 filed Apr. 28, 2021, 21172723.5 filed May 7, 2021 and 21209332.2 filed Nov. 19, 2021, the disclosures of which are incorporated herein by reference in their entirety.

BACKGROUND OF THE INVENTION

The present invention relates to antibodies having specificity to Nectin-4 and uses thereof.

Nectins are adhesion molecules that help organize epithelial and endothelial junctions and serve as receptors for the entry of the herpes simplex virus, measle virus and poliovirus.

Nectins belong to the immunoglobulin superfamily and are homologs of the poliovirus receptor (PVR/CD155), and for this, have also been called poliovirus receptor bound proteins (PRR). To date, 5 members have been described PVR/CD155, Nectin-1/PRR1/CD111, Nectin-2/PRR2/CD112, Nectin-3/PRR3 and Nectin-4/PRR4 (1,10-13). Their ectodomain is made up of three immunoglobulin-like (Ig)-type V, C, C domains that share between 30 and 55% identity in their amino acid sequences.

Expression of Nectin/PRR molecules is generally extensive in tissues, including hematopoietic, neuronal, endothelial and epithelial cells, with the exception of Nectin-3 and -4, which exhibit more restricted expression profiles.

Nectin-4 is a particularly interesting target. It is expressed during fetal development, but its expression decreases and is very restricted in adult tissues in comparison to that of other members of the Nectin family. Nectin-4 is a tumor associated antigen in 83% of bladder cancers, 78% of breast cancers (mainly triple negative and ERBB2+), 71% Pancreatic cancers, 55% of lung cancers, 57% of ovarian cancers, 59% of head and neck cancers, and 55% of esophageal cancers.

Expression of Nectin-4 in these pathologies is associated with poor prognosis, probably as a consequence of the ability of Nectin-4 to confer to tumor cells in vitro, higher capacities of migration, proliferation and formation of metastases. In normal tissues, Nectin-4 is only detected in skin, salivary glands, urinary bladder and esophagus. The recent approval by heath authorities of Enfortumab vedotin for the 2$^{nd}$ line treatment of advanced urothelial cancer has completed the validation of Nectin-4 as a target for the treatment of cancer.

DETAILED DESCRIPTION OF THE INVENTION

The present invention relates to antibodies having specificity to Nectin-4, antigen-binding fragments thereof as well as uses thereof.

In particular, the present invention provides humanized antibodies that derive from the monoclonal anti-Nectin-4 antibody 15A7.5 mAb.

The inventors provide for the first time an antibody, i.e. 15A7.5 mAb, as well as antibodies derived therefrom, specifically binding to Nectin-4 expressed by tumors with a higher affinity in comparison to Nectin-4 expressed by human differentiated keratinocytes. In vitro, this selectivity provides mAb 15A7.5 with lower binding affinity, internalization and cytotoxic activity towards keratinocytes in comparison to tumor cells and in reference to the activity of the HA22 mAb (Enfortumab), in the same assays.

In vivo, this low binding capacity to keratinocytes endows mAb 15A7.5 with a higher half-life due to a lower absorption rate in the skin.

In a xenograft mouse model, treatment with a single dose I.V. of 4 mg/kg of mAb conjugated with Exatecan of established tumors led to a rapid and long-lasting regression.

More particularly, the inventors demonstrate that, in such configuration, 15A7.5 is more efficient than a surrogate of Enfortumab vedotin, i.e., an Enfortumab vedotin product manufactured using non-GMP methods by a third party that is indistinguishable from the commercially available Enfortumab vedotin.

Accordingly, the antibody 15A7.5 and, in particular, humanized variants derived therefrom, thus represents a new way to improve therapeutic index of Nectin-4 positive cancer treatment through lower associated skin toxicity and higher anti-tumor selectivity and efficacy.

Thus, a first aspect of the invention relates to a monoclonal antibody or an antigen-binding fragment thereof which bind to Nectin-4 characterized by a VH region and optionally a VL region each comprising 3 CDRs designated as CDR-H1, CDR-H2, CDR-H3, CDR-L1, CDR-L2 and CDR-L3 defining the binding specificity of the antibody or the antigen-binding antibody fragment. A binding to human Nectin-4 is preferred.

The antibodies of the invention are monoclonal antibodies (mAb) or monoclonal antibody fragments characterized by a specific amino acid sequence. If not indicated differently, the term "monoclonal" refers to a single species, i.e. single amino acid composition of antibodies or antibody fragments.

The antigen-binding site of an inventive antibody comprises heavy chain variable domains/regions (VH) and/or antibody light chain variable domains/regions (VL), or pairs of VH/VL. The variable domains/region denote each of the pair of light and heavy chains which is involved directly in binding the antibody to the antigen. The variable domain of a heavy chain is abbreviated as "VH" and the variable domain of a light chain is abbreviated as "VL".

The term "antigen-binding site" denotes the region(s) of an antibody molecule to which a ligand (e.g. the antigen, i.e. Nectin-4, or antigen fragment of it) actually binds and which is derived from an antibody.

An antigen-binding site of an antibody according to the invention can contain six complementarity determining regions (CDRs) which contribute in varying degrees to the affinity of the binding site for the antigen. There are three heavy chain variable domain CDRs (CDR-H1, CDR-H2 and CDR-H3) and three light chain variable domain CDRs (CDR-L1, CDR-L2 and CDR-L3). Also included within the scope of the invention are functional antigen binding sites comprised of fewer CDRs (i.e., where binding specificity is determined by three, four or five CDRs). For example, less than a complete set of 6 CDRs may be sufficient for binding. In some cases, a VH or a VL domain will be sufficient.

According to the present invention, a VH region or the CDRs thereof alone may constitute a complete antigen-binding site. In certain embodiments, the antibody comprises a VH region or the CDRs thereof as defined herein alone. In other embodiments, the antibody comprises a VH region or the CDRs thereof as defined herein together with a VL region or the CDRs thereof, particularly with a VL region or the CDRs thereof as defined herein.

The position of CDRs within a VH or VL region may be defined according to Kabat, et al., Sequences of Proteins of Immunological Interest, 5th Ed. Public Health Service, National Institutes of Health, Bethesda, MD (1991) or the IMGT numbering system, both of which are known to the person skilled in the art. The IMGT numbering has been defined to compare the variable domains whatever the antigen receptor, the chain type, or the species (Lefranc M.-P., "Unique database numbering system for immunogenetic analysis" Immunology Today, 18, 509 (1997); Lefranc M.-P., "The IMGT unique numbering for Immunoglobulins, T cell receptors and Ig-like domains" The Immunologist, 7, 132-136 (1999)).

A further aspect of the present invention relates to a monoclonal antibody or antigen-binding fragment thereof which binds to Nectin-4 comprising
(a) a variable heavy chain (VH) region comprising complementarity-determining regions (CDRs) CDR-H1, CDR-H2 and CDR-H3, wherein
   (i) the CDR-H1 comprises an amino acid sequence according to SEQ ID NO: 1 or 7,
      or an amino acid sequence comprising a substitution, particularly a conservative substitution of 1 or 2 amino acids,
   (ii) the CDR-H2 comprises an amino acid sequence according to SEQ ID NO: 2 or 8,
      or an amino acid sequence comprising a substitution, particularly a conservative substitution of 1 or 2 amino acids,
   (iii) the CDR-H3 comprises an amino acid sequence according to SEQ ID NO: 3 or 9,
      or a an amino acid sequence comprising a substitution, particularly a conservative substitution of 1 or 2 amino acids, and optionally
(b) a variable light chain (VL) region, particularly a VL region comprising complementarity-determining regions (CDRs) CDR-L1, CDR-L2 and CDR-L3, wherein
   (i) the CDR-L1 comprises an amino acid sequence according to SEQ ID NO: 4 or 10,
      or an amino acid sequence comprising a substitution, particularly a conservative substitution of 1 or 2 amino acids,
   (ii) the CDR-L2 comprises an amino acid sequence according to SEQ ID NO: 5 or 11,
      or an amino acid sequence comprising a substitution, particularly a conservative substitution of 1 or 2 amino acids,
   (iii) the CDR-L3 comprises an amino acid sequence according to SEQ ID NO: 6 or 12,
      or an amino acid sequence comprising a substitution, particularly a conservative substitution of 1 or 2 amino acids.

Specific amino acid sequences represented by SEQ ID NO:s used herein are provided in the attached sequence listing. SEQ ID NO: 1-6 define the six CDR sequences of the inventive parental antibody according to the IMGT numbering system. SEQ ID NO: 7-12 define the six CDR sequences of the inventive parental antibody according to Kabat. If not stated otherwise, the Kabat system is used herein.

According to the present invention, a substitution of 1 or 2 amino acids in these CDR sequences is possible. In particular embodiments, a conservative amino acid substitution is preferable, i.e. a substitution of an amino acid by another amino acid with similar biochemical properties, for example a substitution of an aliphatic amino acid, e.g. Gly, Ala, Val, Leu or Ile, for another aliphatic amino acid, a basic amino acid, e.g. His, Lys or Arg, against another basic amino acid, an acidic amino acid or an amide thereof, e.g. Asp, Glu, Asn or Gln, against another acidic amino acid or an amide thereof, an aromatic amino acid, e.g. Phe, Tyr or Trp, against another aromatic amino acid, or a hydroxy or sulfur containing amino acid, e.g. Ser, Thr, Met or Cys, against another hydroxy or sulfur containing amino acid.

An "antigen-binding fragment" of an antibody refers to a molecule comprising a portion of an intact antibody that binds the antigen to which the intact antibody binds. Examples of antibody fragments include but are not limited to Fv, Fab, Fab', Fab'-SH, F(ab')2; diabodies; linear antibodies; single-chain antibody molecules (e.g. scFv); and multi-specific antibodies formed from antibody fragments. The term also encompasses a fusion protein, e.g. a fusion protein with a non-immunoglobulin peptide or polypeptide, and a conjugate with a nonproteinaceous structure, e.g. a label or a toxin. The terms "antigen-binding fragment of an antibody", "antigen-binding fragment thereof", "fragment of an antibody" or "fragment thereof" may be used interchangeably herein.

The inventive antibody or the antigen-binding fragment thereof may be mono- or multivalent, i.e. it may comprise a single antigen-binding site or multiple antigen-binding sites. For example, Fab fragments have single antigen-binding site, antibodies of the IgG class or Fv or scFv fragments have two antigen-binding sites and antibodies of the IgM class have 5 antigen-binding sites. The term "antibody" also encompasses hetero-specific antibodies, e.g. hetero-bispecific antibodies, which have different antigen-binding sites, particularly antibodies, which are directed to two different epitopes on the antigen. As used herein, "epitope" is a region of an antigen that is bound by an antibody. The term "epitope" includes any polypeptide determinant capable of specific binding to an antibody.

According to a further preferred embodiment, the antibody or antigen-binding fragment thereof comprises according to the IMGT numbering system
   (i) a VH region comprising the CDR-H1 of SEQ ID NO:1, the CDR-H2 of SEQ ID NO:2, and the CDR-H3 of SEQ ID NO:3, and optionally
   (ii) a VL region comprising the CDR-L1 of SEQ ID NO:4, the CDR-L2 of the SEQ ID NO:5 and the CDR-L3 of the SEQ ID NO:6.

According to another preferred embodiment, the antibody or antigen-binding fragment thereof comprises according to Kabat
   (i) a VH region comprising the CDR-H1 of SEQ ID NO:7, the CDR-H2 of SEQ ID NO:8, and the CDR-H3 of SEQ ID NO:9, and optionally
   (ii) a VL region comprising the CDR-L1 of SEQ ID NO:10, the CDR-L2 of the SEQ ID NO:11 and the CDR-L3 of the SEQ ID NO:12.

More particularly, the antibody or antigen-binding fragment thereof may comprise
(a) a VH region comprising an amino acid sequence according to SEQ ID NO:13 or an amino acid sequence having an identity thereof of at least 85%, at least 90%, at least 95% or at least 99% over the whole length of the sequence,
and optionally
(b) a VL region, particularly a VL region comprising an amino acid sequence according to SEQ ID NO:14 or an amino sequence having an identity thereof of at least 85%, at least 90%, at least 95% or at least 99% over the whole length of the sequence.

"Percent (%) amino acid sequence identity" with respect to a peptide or polypeptide sequence is defined as the percentage of amino acid residues in a candidate sequence that are identical with the amino acid residues in the specific peptide or polypeptide sequence, after aligning the sequences and introducing gaps, if necessary, to achieve the maximum percent sequence identity, Alignment for purposes of determining percent amino acid sequence identity can be achieved in various ways that are within the skill in the art, for instance, using publicly available computer software such as BLAST.

The antibody of the invention may be a chimeric antibody, a multispecific antibody, in particular a bispecific antibody, a human antibody, a humanized antibody or an antigen-binding fragment thereof.

According to the present invention, a "chimeric" antibody refers to an antibody in which a portion of the heavy and/or light chain is derived from a particular source or species, while the remainder of the heavy and/or light chain is derived from a different source or species.

"Multispecific antibodies" bind two or more different epitopes. The epitopes may be on the same or different antigens. A preferred example of a multi-specific antibody is a "bispecific antibody" which binds two different epitopes In preferred embodiments, the antibody of the invention is a humanized antibody.

The term "humanized antibody" or "humanized version of an antibody" refers to antibodies for which both heavy and light chains are humanized as a result of antibody engineering. A humanized chain is typically a chain in which the V-region amino acid sequence has been changed so that, analyzed as a whole, is closer in homology to a human germ line sequence than to the germ line sequence of the species of origin. For example, a murine CDR may be grafted into the framework region of a human antibody to prepare the "humanized antibody." See, e.g., Riechmann, L., et al., Nature 332 (1988) 323-327; and Neuberger, M. S., et al., Nature 314 (1985) 268-270. Other forms of humanized antibodies encompassed by the present invention are those in which the constant region has been additionally modified or changed from that of the original antibody to generate the properties according to the invention. Humanization assessment is based on the resulting amino acid sequence and not on the methodology per se.

Another preferred embodiment refers to human antibodies.

The term "human antibody", as used herein, is intended to include antibodies having variable and constant regions derived from human germ line immunoglobulin sequences. Human antibodies are well-known in the state of the art (van Dijk, M. A., and van de Winkel, J. G., Curr. Opin. Chem. Biol. 5 (2001) 368-374). Human antibodies can also be produced in transgenic animals (e.g., mice) that are capable, upon immunization, of producing a full repertoire or a selection of human antibodies in the absence of endogenous immunoglobulin production.

The antibody of the present invention may be of any suitable class. The term "class" refers to the type of constant domain or constant region possessed by its heavy chain. As used herein, "constant domain" or "constant region" denotes the sum of the domains of an antibody other than the variable region. The constant region is not directly involved in binding of an antigen, but exhibits various effector functions. The antibody may be of any of the five major classes of antibodies: IgA, IgD, IgE, IgG, and IgM, or any subclass thereof (isotype), e.g., IgG1, IgG2, IgG3, IgG4, IgA1, and IgA2. The heavy chain constant domains that correspond to the different classes of immunoglobulins are called α, δ, ε, γ and μ, respectively. According to the present invention, an antibody of the class IgG, IgA or IgM or a fragment thereof is particularly suitable.

According to a preferred embodiment, an antibody of the invention is selected from class IgG, e.g. of subclass IgG1, IgG2, IgG3 of IgG4, of class IgM, of class IgA or an antigen-binding fragment thereof.

In particular embodiments, the inventive humanized or human antibodies are defined by combination of at least 3, preferably 6, complementarity-determining regions (CDRs), i.e. relate to antibodies or antigen-binding fragments thereof comprising (a) a variable heavy chain (VH) region comprising complementarity-determining regions (CDRs) CDR-H1, CDR-H2 and CDR-H3, wherein
  (i) the CDR-H1 comprises an amino acid sequence according to SEQ ID NO: 21, 35, 49 or 63,
    or an amino acid sequence comprising a substitution, particularly a conservative substitution of 1 or 2 amino acids,
  (ii) the CDR-H2 comprises an amino acid sequence according to SEQ ID NO: 22, 36, 50 or 64
    or an amino acid sequence comprising a substitution, particularly a conservative substitution of 1 or 2 amino acids,
  (iii) the CDR-H3 comprises an amino acid sequence according to SEQ ID NO: 23, 37, 51 or 65,
    or an amino acid sequence comprising a substitution, particularly a conservative substitution of 1 or 2 amino acids, and optionally
(b) a variable light chain (VL) region, particularly a VL region comprising complementarity-determining regions (CDRs) CDR-L1, CDR-L2 and CDR-L3, wherein
  (i) the CDR-L1 comprises an amino acid sequence according to SEQ ID NO: 24, 38, 52 or 66,
    or an amino acid sequence comprising a substitution, particularly a conservative substitution of 1 or 2 amino acids,
  (ii) the CDR-L2 comprises an amino acid sequence according to SEQ ID NO: 25, 39, 53 or 67,
    or an amino acid sequence comprising a substitution, particularly a conservative substitution of 1 or 2 amino acids,
  (iii) the CDR-L3 comprises an amino acid sequence according to SEQ ID NO: 26, 40, 54 or 68,
    or an amino acid sequence comprising a substitution, particularly a conservative substitution of 1 or 2 amino acids.

Specific humanized or human antibodies according to the present invention may comprise
  (a) (i) a VH region comprising the CDR-H1 of SEQ ID NO:21, the CDR-H2 of SEQ ID NO:22, and the CDR-H3 of SEQ ID NO:23,
    and optionally
    (ii) a VL region comprising the CDR-L1 of SEQ ID NO:24, the CDR-L2 of the SEQ ID NO:25, and the CDR-L3 of the SEQ ID NO:26, or
  (b) (i) a VH region comprising the CDR-H1 of SEQ ID NO:35, the CDR-H2 of SEQ ID NO:36, and the CDR-H3 of SEQ ID NO:37,
    and optionally (ii) a VL region comprising the CDR-L1 of SEQ ID NO:38, the CDR-L2 of the SEQ ID NO:39, and the CDR-L3 of the SEQ ID NO:40, or (c) (i) a VH region comprising the CDR-H1 of SEQ ID NO:49, the CDR-H2 of SEQ ID NO:50, and the CDR-H3 of SEQ ID NO:51,
and optionally
(ii) a VL region comprising the CDR-L1 of SEQ ID NO:52, the CDR-L2 of the SEQ ID NO:53, and the CDR-L3 of the SEQ ID NO:54, or (d) (i) a VH region comprising the CDR-H1 of SEQ ID NO:63, the CDR-H2 of SEQ ID NO:64, and the CDR-H3 of SEQ ID NO:65,
and optionally
(ii) a VL region comprising the CDR-L1 of SEQ ID NO:66, the CDR-L2 of the SEQ ID NO:67 and the CDR-L3 of the SEQ ID NO:68, or (e) (i) a VH region comprising the CDR-H1 of SEQ ID NO:21, the CDR-H2 of SEQ ID NO:22, and the CDR-H3 of SEQ ID NO:23,
and optionally
(ii) a VL region comprising the CDR-L1 of SEQ ID NO:38, the CDR-L2 of the SEQ ID NO:39 and the CDR-L3 of the SEQ ID NO:40, or (f) (i) a VH region comprising the CDR-H1 of SEQ ID NO:21, the CDR-H2 of SEQ ID NO:22, and the CDR-H3 of SEQ ID NO:23,
and optionally
(ii) a VL region comprising the CDR-L1 of SEQ ID NO:52, the CDR-L2 of the SEQ ID NO:53 and the CDR-L3 of the SEQ ID NO:54, or (g) (i) a VH region comprising the CDR-H1 of SEQ ID NO:21, the CDR-H2 of SEQ ID NO:22, and the CDR-H3 of SEQ ID NO:23,
and optionally
(ii) a VL region comprising the CDR-L1 of SEQ ID NO:66, the CDR-L2 of the SEQ ID NO:67 and the CDR-L3 of the SEQ ID NO:68, or (h) (i) a VH region comprising the CDR-H1 of SEQ ID NO:35, the CDR-H2 of SEQ ID NO:36, and the CDR-H3 of SEQ ID NO:37,
and optionally
(ii) a VL region comprising the CDR-L1 of SEQ ID NO:24, the CDR-L2 of the SEQ ID NO:25 and the CDR-L3 of the SEQ ID NO:26, or (j) (i) a VH region comprising the CDR-H1 of SEQ ID NO:35, the CDR-H2 of SEQ ID NO:36, and the CDR-H3 of SEQ ID NO:37,
and optionally
(ii) a VL region comprising the CDR-L1 of SEQ ID NO:52, the CDR-L2 of the SEQ ID NO:53 and the CDR-L3 of the SEQ ID NO:54, or (k) (i) a VH region comprising the CDR-H1 of SEQ ID NO:35, the CDR-H2 of SEQ ID NO:36, and the CDR-H3 of SEQ ID NO:37,
and optionally
(ii) a VL region comprising the CDR-L1 of SEQ ID NO:66, the CDR-L2 of the SEQ ID NO:67 and the CDR-L3 of the SEQ ID NO:68, or (l) (i) a VH region comprising the CDR-H1 of SEQ ID NO:49, the CDR-H2 of SEQ ID NO:50, and the CDR-H3 of SEQ ID NO:51,
and optionally
(ii) a VL region comprising the CDR-L1 of SEQ ID NO:24, the CDR-L2 of the SEQ ID NO:25 and the CDR-L3 of the SEQ ID NO:26, or (m) (i) a VH region comprising the CDR-H1 of SEQ ID NO:49, the CDR-H2 of SEQ ID NO:50, and the CDR-H3 of SEQ ID NO:51,
and optionally
(ii) a VL region comprising the CDR-L1 of SEQ ID NO:38, the CDR-L2 of the SEQ ID NO:39 and the CDR-L3 of the SEQ ID NO:40, or (n) (i) a VH region comprising the CDR-H1 of SEQ ID NO:49, the CDR-H2 of SEQ ID NO:50, and the CDR-H3 of SEQ ID NO:51,
and optionally
(ii) a VL region comprising the CDR-L1 of SEQ ID NO:66, the CDR-L2 of the SEQ ID NO:67 and the CDR-L3 of the SEQ ID NO:68, or (o) (i) a VH region comprising the CDR-H1 of SEQ ID NO:63, the CDR-H2 of SEQ ID NO:64, and the CDR-H3 of SEQ ID NO:65,
and optionally
(ii) a VL region comprising the CDR-L1 of SEQ ID NO:24, the CDR-L2 of the SEQ ID NO:25 and the CDR-L3 of the SEQ ID NO:26, or (p) (i) a VH region comprising the CDR-H1 of SEQ ID NO:63, the CDR-H2 of SEQ ID NO:64, and the CDR-H3 of SEQ ID NO:65,
and optionally
(ii) a VL region comprising the CDR-L1 of SEQ ID NO:38, the CDR-L2 of the SEQ ID NO:39 and the CDR-L3 of the SEQ ID NO:40, or (q) (i) a VH region comprising the CDR-H1 of SEQ ID NO:63, the CDR-H2 of SEQ ID NO:64, and the CDR-H3 of SEQ ID NO:65,
and optionally
(ii) a VL region comprising the CDR-L1 of SEQ ID NO:52, the CDR-L2 of the SEQ ID NO:53 and the CDR-L3 of the SEQ ID NO:54.

In particular preferred are the humanized antibodies (a), (b), (c), (d), (j), (k), (n) and (q) as defined above.

Of course, the humanized or human antibodies according to the invention may be also defined by their VH and/or VL regions.

Such antibodies may comprise
(i) a VH region comprising an amino acid sequence selected from SEQ ID NO:27, 41, 55 or 69 or an amino acid sequence having an identity thereof of at least 85%, at least 90%, at least 95% or at least 99%,
and optionally
(ii) a VL region, particularly a VL region comprising an amino acid sequence selected from SEQ ID NO:28, 42, 56, 70 or 103 or an amino sequence having an identity thereof of at least 85%, at least 90%, at least 95% or at least 99%.

Specific humanized or human antibodies according to the invention may be defined by their VH and/or VL regions, wherein such antibodies comprise
(a) (i) a VH region comprising an amino acid sequence according to SEQ ID NO:27 or an amino acid sequence having an identity thereof of at least 85%, at least 90%, at least 95% or at least 99%,
and optionally
(ii) a VL region, particularly a VL region comprising an amino acid sequence according to SEQ ID NO:28 or an amino sequence having an identity thereof of at least 85%, at least 90%, at least 95% or at least 99%, or (b) (i) a VH region comprising an amino acid sequence according to SEQ ID NO:41 or an amino acid sequence having an identity thereof of at least 85%, at least 90%, at least 95% or at least 99%,
and optionally
  (ii) a VL region, particularly a VL region comprising an amino acid sequence according to SEQ ID NO:42 or an amino sequence having an identity thereof of at least 85%, at least 90%, at least 95% or at least 99%,
  or
(c) (i) a VH region comprising an amino acid sequence according to SEQ ID N0:55 or an amino acid sequence having an identity thereof of at least 85%, at least 90%, at least 95% or at least 99%,
and optionally
  (ii) a VL region, particularly a VL region comprising an amino acid sequence according to SEQ ID NO:56 or an amino sequence having an identity thereof of at least 85%, at least 90%, at least 95% or at least 99%,
  or
(d) (i) a VH region comprising an amino acid sequence according to SEQ ID NO:69 or an amino acid sequence having an identity thereof of at least 85%, at least 90%, at least 95% or at least 99%,
and optionally
  (ii) a VL region, particularly a VL region comprising an amino acid sequence according to SEQ ID NO:70 or 103 or an amino sequence having an identity thereof of at least 85%, at least 90%, at least 95% or at least 99%,
  or
(e) (i) a VH region comprising an amino acid sequence according to SEQ ID NO:27 or an amino acid sequence having an identity thereof of at least 85%, at least 90%, at least 95% or at least 99%,
and optionally
  (ii) a VL region, particularly a VL region comprising an amino acid sequence according to SEQ ID NO:42 or an amino sequence having an identity thereof of at least 85%, at least 90%, at least 95% or at least 99%,
  or
(f) (i) a VH region comprising an amino acid sequence according to SEQ ID NO:27 or an amino acid sequence having an identity thereof of at least 85%, at least 90%, at least 95% or at least 99%,
and optionally
  (ii) a VL region, particularly a VL region comprising an amino acid sequence according to SEQ ID NO:56 or an amino sequence having an identity thereof of at least 85%, at least 90%, at least 95% or at least 99%,
  or
(g) (i) a VH region comprising an amino acid sequence according to SEQ ID NO:27 or an amino acid sequence having an identity thereof of at least 85%, at least 90%, at least 95% or at least 99%,
and optionally
  (ii) a VL region, particularly a VL region comprising an amino acid sequence according to SEQ ID NO:70 or 103 or an amino sequence having an identity thereof of at least 85%, at least 90%, at least 95% or at least 99%,
  or
(h) (i) a VH region comprising an amino acid sequence according to SEQ ID NO:41 or an amino acid sequence having an identity thereof of at least 85%, at least 90%, at least 95% or at least 99%, and optionally
  (ii) a VL region, particularly a VL region comprising an amino acid sequence according to SEQ ID NO:28 or an amino sequence having an identity thereof of at least 85%, at least 90%, at least 95% or at least 99%,
  or
(j) (i) a VH region comprising an amino acid sequence according to SEQ ID NO:41 or an amino acid sequence having an identity thereof of at least 85%, at least 90%, at least 95% or at least 99%,
and optionally
  (ii) a VL region, particularly a VL region comprising an amino acid sequence according to SEQ ID NO:56 or an amino sequence having an identity thereof of at least 85%, at least 90%, at least 95% or at least 99%,
  or
(k) (i) a VH region comprising an amino acid sequence according to SEQ ID NO:41 or an amino acid sequence having an identity thereof of at least 85%, at least 90%, at least 95% or at least 99%,
and optionally
  (ii) a VL region, particularly a VL region comprising an amino acid sequence according to SEQ ID NO:70 or 103 or an amino sequence having an identity thereof of at least 85%, at least 90%, at least 95% or at least 99%,
  or
(l) (i) a VH region comprising an amino acid sequence according to SEQ ID NO:55 or an amino acid sequence having an identity thereof of at least 85%, at least 90%, at least 95% or at least 99%,
and optionally
  (ii) a VL region, particularly a VL region comprising an amino acid sequence according to SEQ ID NO:28 or an amino sequence having an identity thereof of at least 85%, at least 90%, at least 95% or at least 99%,
  or
(m) (i) a VH region comprising an amino acid sequence according to SEQ ID NO:55 or an amino acid sequence having an identity thereof of at least 85%, at least 90%, at least 95% or at least 99%,
and optionally
  (ii) a VL region, particularly a VL region comprising an amino acid sequence according to SEQ ID NO:42 or an amino sequence having an identity thereof of at least 85%, at least 90%, at least 95% or at least 99%,
  or
(n) (i) a VH region comprising an amino acid sequence according to SEQ ID NO:55 or an amino acid sequence having an identity thereof of at least 85%, at least 90%, at least 95% or at least 99%,
and optionally
  (ii) a VL region, particularly a VL region comprising an amino acid sequence according to SEQ ID NO:70 or 103 or an amino sequence having an identity thereof of at least 85%, at least 90%, at least 95% or at least 99%,
(o) (i) a VH region comprising an amino acid sequence according to SEQ ID NO:69 or an amino acid sequence having an identity thereof of at least 85%, at least 90%, at least 95% or at least 99%,
and optionally
  (ii) a VL region, particularly a VL region comprising an amino acid sequence according to SEQ ID NO:28 or an amino sequence having an identity thereof of at least 85%, at least 90%, at least 95% or at least 99%,
  or
(p) (i) a VH region comprising an amino acid sequence according to SEQ ID NO:69 or an amino acid sequence having an identity thereof of at least 85%, at least 90%, at least 95% or at least 99%,
and optionally
(ii) a VL region, particularly a VL region comprising an amino acid sequence according to SEQ ID NO:42 or an amino sequence having an identity thereof of at least 85%, at least 90%, at least 95% or at least 99%,
or
(q) (i) a VH region comprising an amino acid sequence according to SEQ ID NO:69 or an amino acid sequence having an identity thereof of at least 85%, at least 90%, at least 95% or at least 99%,
and optionally
(ii) a VL region, particularly a VL region comprising an amino acid sequence according to SEQ ID NO:56 or an amino sequence having an identity thereof of at least 85%, at least 90%, at least 95% or at least 99%.

In particular preferred are the humanized antibodies (a), (b), (c), (d), (j), (k), (n) and (q) as defined above.

According to an especially preferred embodiment, the inventive antibodies and antigen-binding fragments thereof bind to Nectin-4 expressed by tumors with a higher affinity in comparison to Nectin-4 expressed by human differentiated keratinocytes. Such specific binding allows, inter alia, less side effects, in particular reduced skin toxicity, during a treatment based on the inventive antibodies.

As used herein, the terms "binding" and "specific binding" refer to the binding of the inventive antibody or fragment thereof to an epitope of the Nectin-4 antigen. The measure of the binding strength of an antibody is referred to as affinity. Methods for determining such a binding and/or affinity using in vitro assays are known to the person skilled in the art. According to the present invention, detection with flow cytometry, immuno-histochemistry and/or fluorescence are described and in particular preferred herein.

The affinity of the binding of an antibody to an antigen is defined by the terms Ka (rate constant for the association of the antibody from the antibody/antigen complex), KD (dissociation constant), and $K_{dis}$ (kD/ka).

Antibodies according to the invention and antigen-binding fragments thereof preferably show a dissociation constant KD of at least 40, preferably at least more preferably at least 50 and most preferably at least 55 (nM).

An especially preferred embodiment of the invention relates to a humanized antibody and antigen-binding fragments thereof, comprising
(i) a VH region comprising the CDR-H1 of SEQ ID NO:1, the CDR-H2 of SEQ ID NO:2, and the CDR-H3 of SEQ ID NO:3, and optionally
(ii) a VL region comprising the CDR-L1 of SEQ ID NO:4, the CDR-L2 of the SEQ ID NO:5 and the CDR-L3 of the SEQ ID NO:6,
wherein the antibody and antigen-binding fragments thereof bind to Nectin-4 expressed by tumors with a higher affinity in comparison to Nectin-4 expressed by human differentiated keratinocytes.

Further aspects of the present invention relate to the monoclonal anti-Nectin-4 antibodies 9A2.7, 3A1.4 as well as 8F06 and antigen-binding fragments thereof as described herein. Humanized variants of those antibodies are preferred.

Thus, the present invention also provides monoclonal antibodies or antigen-binding fragment thereof which bind to Nectin-4 comprising
(a) a variable heavy chain (VH) region comprising complementarity-determining regions (CDRs) CDR-H1, CDR-H2 and CDR-H3, wherein
(i) the CDR-H1 comprises an amino acid sequence according to SEQ ID NO:79, 87 or 95,
or an amino acid sequence comprising a substitution, particularly a conservative substitution of 1 or 2 amino acids,
(ii) the CDR-H2 comprises an amino acid sequence according to SEQ ID NO:80, 88 or 96,
or an amino acid sequence comprising a substitution, particularly a conservative substitution of 1 or 2 amino acids,
(iii) the CDR-H3 comprises an amino acid sequence according to SEQ ID NO:81, 89 or 97,
or a an amino acid sequence comprising a substitution, particularly a conservative substitution of 1 or 2 amino acids, and optionally
(b) a variable light chain (VL) region, particularly a VL region comprising complementarity-determining regions (CDRs) CDR-L1, CDR-L2 and CDR-L3, wherein
(i) the CDR-L1 comprises an amino acid sequence according to SEQ ID NO:83, 91 or 99,
or an amino acid sequence comprising a substitution, particularly a conservative substitution of 1 or 2 amino acids,
(ii) the CDR-L2 comprises an amino acid sequence according to SEQ ID NO:84, 92 or 100
or an amino acid sequence comprising a substitution, particularly a conservative substitution of 1 or 2 amino acids,
(iii) the CDR-L3 comprises an amino acid sequence according to SEQ ID NO:85, 93 or 101.
or an amino acid sequence comprising a substitution, particularly a conservative substitution of 1 or 2 amino acids.

One embodiment, relates to an anti-Nectin 4 antibody or antigen-binding fragment thereof comprising
(i) a VH region comprising the CDR-H1 of SEQ ID NO:79, the CDR-H2 of SEQ ID NO:80, and the CDR-H3 of SEQ ID NO:81, and optionally
(ii) a VL region comprising the CDR-L1 of SEQ ID NO:83, the CDR-L2 of the SEQ ID NO:84 and the CDR-L3 of the SEQ ID NO:85;
or
(a) a VH region comprising an amino acid sequence according to SEQ ID NO:82 or an amino acid sequence having an identity thereof of at least 85%, at least 90%, at least 95% or at least 99%, and optionally
(b) a VL region, particularly a VL region comprising an amino acid sequence according to SEQ ID NO:86 or an amino sequence having an identity thereof of at least 85%, at least 90%, at least 95% or at least 99%.

Antibody 9A2.7 is characterized by such VH region and VL region sequences.

One embodiment, relates to an anti-Nectin 4 antibody or antigen-binding fragment thereof comprising
(i) a VH region comprising the CDR-H1 of SEQ ID NO:87, the CDR-H2 of SEQ ID NO:88, and the CDR-H3 of SEQ ID NO:89, and optionally
(ii) a VL region comprising the CDR-L1 of SEQ ID NO:91, the CDR-L2 of the SEQ ID NO:92 and the CDR-L3 of the SEQ ID NO:93;
or
(a) a VH region comprising an amino acid sequence according to SEQ ID NO:90 or an amino acid sequence having an identity thereof of at least 85%, at least 90%, at least 95% or at least 99%, and optionally (b) a VL region, particularly a VL region comprising an amino acid sequence according to SEQ ID NO:94 or an amino sequence having an identity thereof of at least 85%, at least 90%, at least 95% or at least 99%.

Antibody 3A1.4 is characterized by such VH region and VL region sequences.

One embodiment, relates to an anti-Nectin 4 antibody or antigen-binding fragment thereof comprising
(i) a VH region comprising the CDR-H1 of SEQ ID NO:95, the CDR-H2 of SEQ ID NO:96, and the CDR-H3 of SEQ ID NO:97, and optionally
(ii) a VL region comprising the CDR-L1 of SEQ ID NO:99, the CDR-L2 of the SEQ ID NO:100 and the CDR-L3 of the SEQ ID NO:101;
or
(a) a VH region comprising an amino acid sequence according to SEQ ID NO:98 or an amino acid sequence having an identity thereof of at least 85%, at least 90%, at least 95% or at least 99%, and optionally
(b) a VL region, particularly a VL region comprising an amino acid sequence according to SEQ ID NO:102 or an amino sequence having an identity thereof of at least 85%, at least 90%, at least 95% or at least 99%.

Antibody 8F06 is characterized by such VH region and VL region sequences.

SEQ ID NO:s 79-86 characterize mAb 9A2.7.
SEQ ID NO:s 87-94 characterize mAb 3A1.4.
SEQ ID NO:s 95-102 characterize mAb 8F06.

Beside a lower binding affinity, the inventive antibodies and fragments provided herein show also preferably lower internalization and/or cytotoxic activity towards keratinocytes in comparison to tumor cells.

According to an especially preferred embodiment, the inventive antibodies and fragments show lower binding affinity, lower internalization and lower cytotoxic activity towards keratinocytes in comparison to tumor cells.

Of course, a specific binding to human Nectin-4 expressed by tumors is preferred. Thus, the antibodies provided herein show preferably specific binding to Nectin-4 and no essential or no cross reactivity to other proteins, in particular to proteins of the human Nectin-family such as Nectin-1.

According to a further aspect, the present invention also relates to a monoclonal antibody or antigen-binding fragment thereof characterized by binding to human Nectin-4 expressed by tumors with a higher affinity in comparison to Nectin-4 expressed by human differentiated keratinocytes. For comparison, the binding affinity may be detected by flow cytometry, immuno-histochemistry and/or fluorescence.

According to a further embodiment, inventive antibodies or antigen-binding fragments thereof comprise a labeling group and/or an effector group being coupled to the antibody or antigen-binding fragment. The labeling group may be, for example, a dye, a paramagnetic, radioactive or fluorogenic group that is detectable upon imaging. A preferred effector group is a therapeutic group, in particular a cytotoxic agent, such as chemotherapeutically active agents, drugs, anti-inflammatory agents, radioactive isotopes, toxins such as topoisomerase poisons, enzymes and fragments thereof such as nucleolytic enzymes, growth inhibitory agents, antibiotics as wells as all suitable anticancer and antitumor agents known to the person skilled in the art. Especially preferred is the topoisomerase poison Camptothecin and derivatives and/or structural analogues thereof like Exatecan as well as derivatives thereof like Deruxtecan.

A preferred embodiment of an antitumor agent relates to antitumor immune stimulating agents including but not restricted to toll-like receptor (TLR) agonists or stimulators of interferon genes (STING) pathways.

According to another preferred embodiment an anti-inflammatory agent may be selected from group comprising steroids and corticosteroids such as glucocorticoids, e.g. cortisol and derivatives thereof, or mineralocorticoids such as aldosterone and derivatives thereof.

According to a further aspect of the invention, the antibody or antigen-binding fragment thereof is for use in medicine, particularly for therapeutic or diagnostic applications including in vitro and in vivo diagnostic applications.

The antibody or antigen-binding fragment thereof may be of use in a method of preventing and/or treating cancer and/or inflammatory disorders, wherein the cancer and/or inflammatory disorder is preferably associated with Nectin-4 overexpression.

The cancer to be prevented and/or treated may be any kind of cancer, wherein the term "cancer" is used herein to refer to proliferative diseases. The cancer to be prevented and/or treated according to the present invention is preferably selected from the group consisting of urothelial, endometrial, cervical, colorectal, liver, bladder, thyroid, breast, pancreatic, lung, ovarian head and neck and/or esophagus cancer.

Being highly specific for Nectin-4 expressed on tumors, the inventive antibodies and fragments thereof may be also used in diagnostics, for example being coupled to a labeling group as described above.

According to a further aspect, the antibody or antigen-binding fragment thereof as described herein may be used in a method of preventing and/or treating an inflammatory disorder, wherein the inflammatory disorder is preferably associated with Nectin-4 expression. Such treatment may be preferably combined with an anti-inflammatory agent known to the person skilled in the art. Preferred anti-inflammatory agents are described above.

Another aspect of the present invention is a combination of at least 2 different monoclonal antibodies or fragments as described herein.

Further, the present invention relates to a nucleic acid molecule, e.g. a DNA molecule, encoding an antibody VH region, or an antibody VL region, or encoding a complete antibody or an antibody fragment as indicated above, a vector or vector system, i.e. a plurality of vectors, comprising said nucleic acid molecule(s) as indicated above, preferably in operative linkage with an expression control sequence, particularly with a heterologous expression control sequence.

Furthermore, the invention relates to a cell comprising a nucleic acid molecule or a vector or vector system as described above. The term "vector," as used herein, refers to a nucleic acid molecule capable of propagating another nucleic acid to which it is linked. According to a preferred embodiment, the vector is an expression vector. An "expression vector" is a vector are capable of directing the expression of nucleic acids to which they are operatively linked.

Vectors, in particular expression vectors, for the recombinant production of antibodies are well known in the art.

The cell may be a known host cell for producing antibodies or antibody fragments, e.g. a prokaryotic cell such as an *E. coli* cell, a yeast cell, an insect cell or a mammalian cell, e.g. a CHO cell or a hybridoma cell.

Still a further aspect of the present invention relates to a pharmaceutical composition comprising an antibody or antigen-binding fragment thereof as described herein. Typically, the antibody or antibody-fragment is administered as a pharmaceutical composition comprising the active agent and a pharmaceutically acceptable carrier or excipient. Examples of suitable carriers and excipients for formulating antibodies or antibody fragments include saline and aqueous buffer solutions and are well known in the art.

Depending on the stage and the severity of the disorder to be treated, the pharmaceutical composition may be administered once or several times during the course of the disorder. For example, it may be administered daily, each second day, two times weekly or weekly for a suitable period of time.

In certain embodiments, the pharmaceutical composition is administered parenterally, e.g. by subcutaneous, intramuscular or intravenous injection or by infusion. In further embodiments, the pharmaceutical composition may be administered locally, e.g. orally, nasally or pulmonally, for example as an aerosol.

Further, the present invention is explained in more detail by the following Tables, Figures and Examples.

FIGURES

FIG. 1: Ch-15A7.5 recognizes human Nectin-4. Detection by flow cytometry.

Flow cytometry analysis of MDA-MB231 transfected with the N-terminal Flag-tagged epitope of Nectin-4 using a dose range (0.3 ng/mL-5 µg/mL) of Ch-15A7 antibody. Parental MDA-MB231 cells are included as controls. Cells were then stained with phycoerythrin conjugate goat anti human Fc antibody. The normalized mean fluorescence intensity is shown. Inlay: staining of parental MDA-MB231 cells with anti Nectin-1, -2 and -3 mAbs (5 µg/mL). Mean fluorescence intensity is represented.

Figure 2:
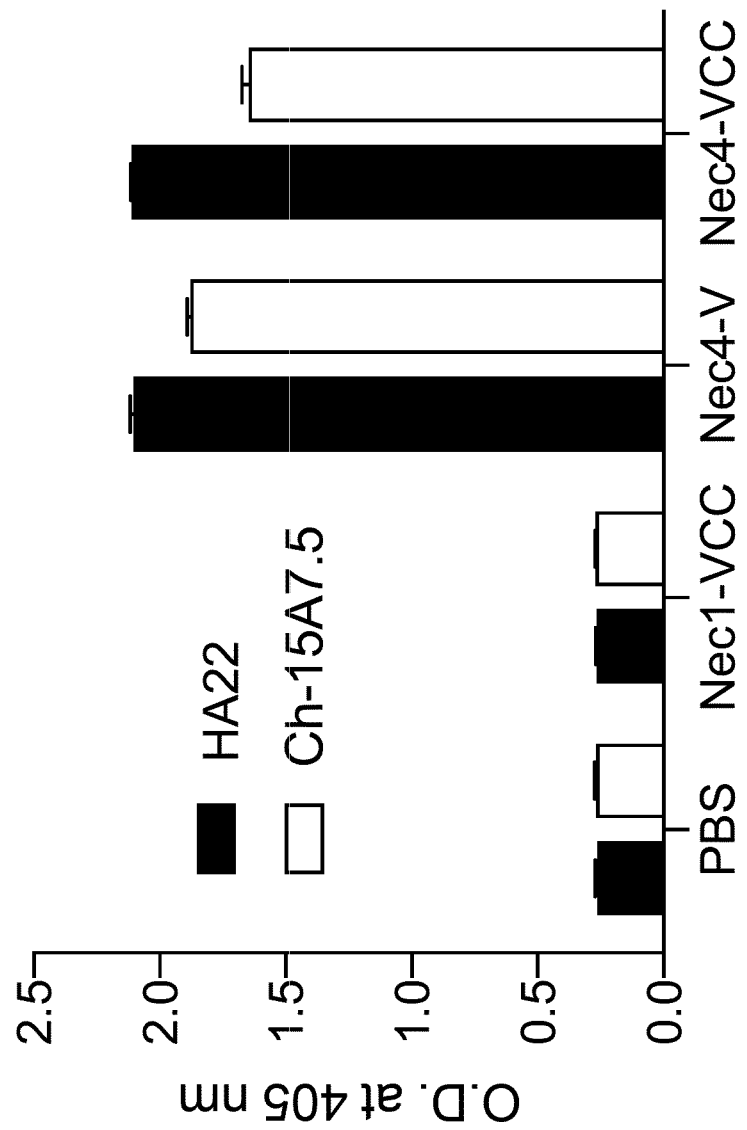

FIG. 2: Ch-15A7.5 recognizes IgV-like domain of human Nectin-4. Detection by ELISA.

Ninety-six-wells plates were coated, as indicated, with 5 µg/mL Nectin-1 extracellular domain Fc fusion recombinant protein (Nec1-VCC), or Nectin-4 IgV-like domain Fc fusion recombinant protein (Nec4-V), or Nectin-4 extracellular domain Fc fusion recombinant protein (Nec4-VCC) overnight at 4° C. Ch15A7.5 recognizes the Nectin-4 extracellular domain, more precisely the Nectin-4 IgV-like domain and not the Nectin-1 extracellular domain.

Figure 3:
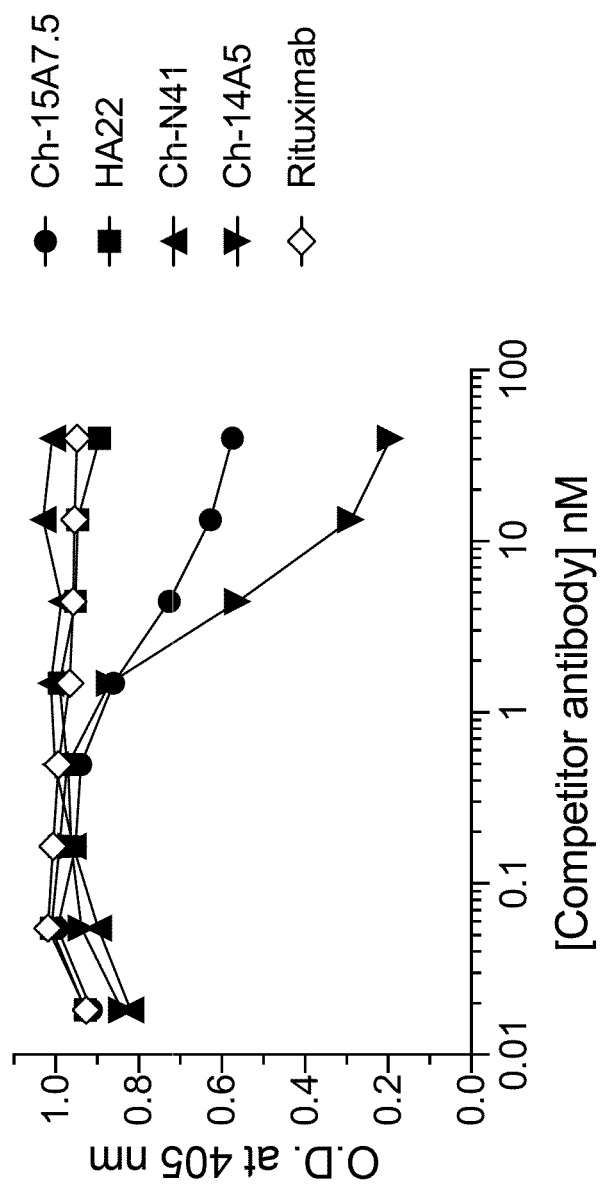

FIG. 3: Characterization of Ch-15A7.5 epitope. Competition assay was performed by ELISA.

Ninety-six-wells plates were coated with 5 µg/mL of Nectin-4 extracellular domain Fc fusion recombinant protein (Nec4-VCC) overnight at 4° C. Binding of peroxidase-conjugated Ch-15A7.5 mAb (5 µg/m L) was measured in presence of increasing concentrations (2.75 ng/mL-6 µg/mL) of Rituximab, Ch-15A7 mAb, Enfortumab (HA22), Ch-N41 mAb and Ch-14A5 mAb. HA22, Ch-N41 and CH-14A5 recognize the IgV domain of Nectin-4.

Figure 4:
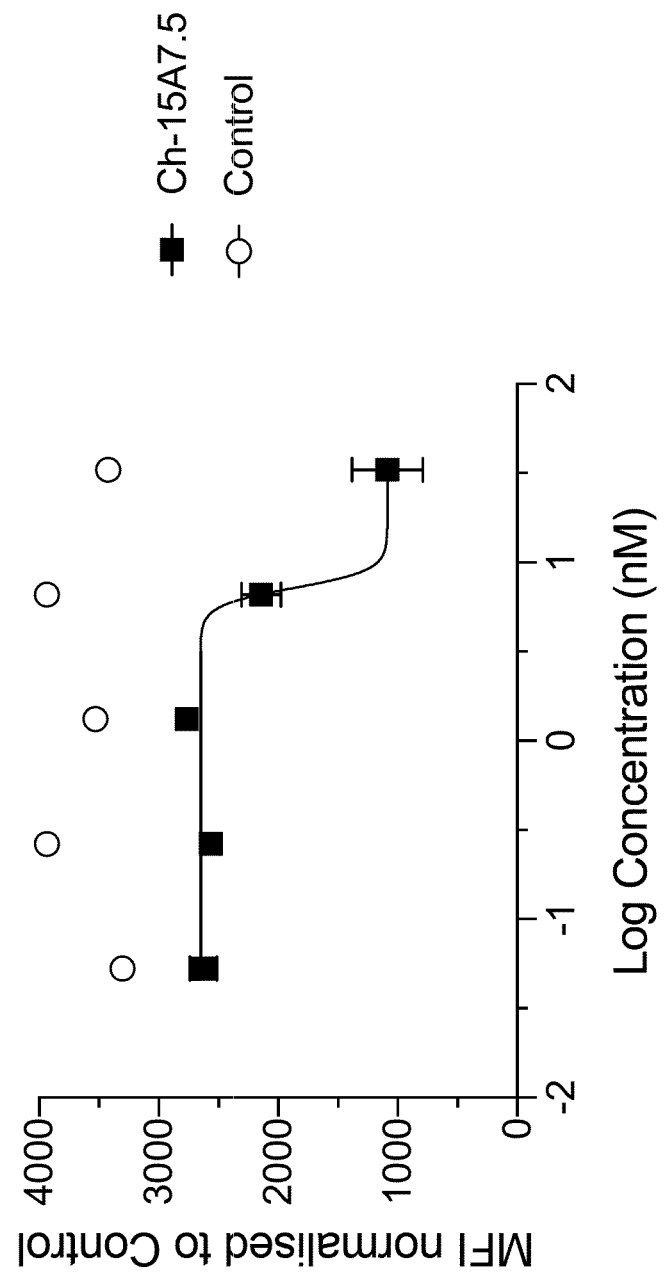

FIG. 4: Competition of Ch-15A7.5 mAb with Nectin-1 for Nectin-4 binding. Competition was assessed by flow cytometry.

Ninety-six-wells plates were seeded with 50,000 CHO cells transfected with human Nectin-4 cDNA. Cells were incubated 45 minutes with increasing concentrations of isotypic control or Ch15A7.5 mAb (8 ng/mL-5 µg/mL). After washing, plates were incubated with 20 µg/mL of Nectin-1 extracellular domain Fc fusion recombinant protein (Nec1-VCC). Nectin-1 binding was revealed after incubation with goat anti human Fc antibody coupled to phycoerythrin.

Figure 5:
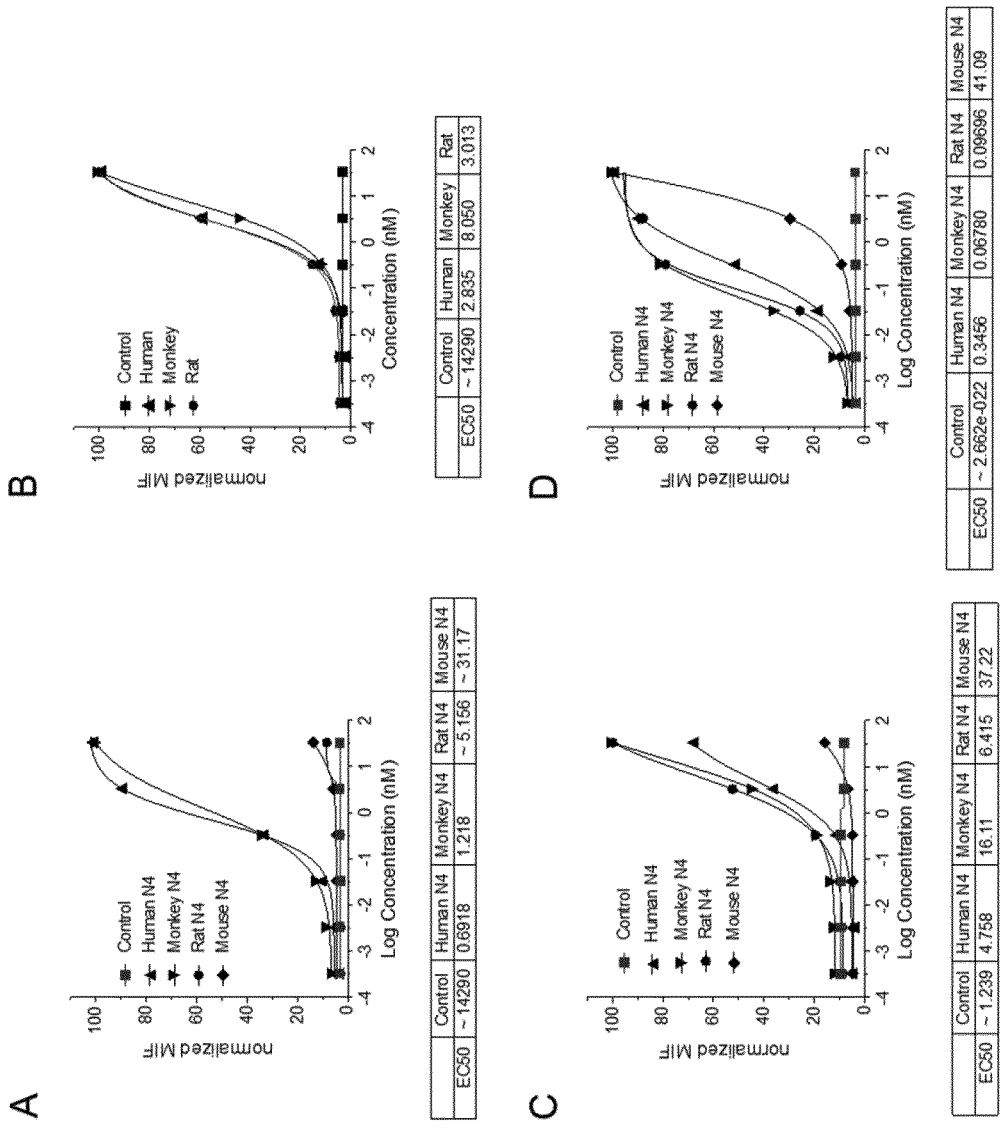

FIG. 5: Cross-reactivity with Nectin-4 from cynomolgus monkey, rat and mouse. Detection by flow cytometry.

Flow cytometry analysis of CHO cells transfected with human, cynomolgus monkey, rat or mouse Nectin-4 using a dose range of Ch-15A7 (A), Ch-3A1.4 (B), Ch-9A2.7 (C) or Enfortumab (HA22, D) antibodies (0.05 ng/mL-5 µg/mL). Cells were then stained with phycoerythrin conjugate goat anti human Fc antibody. Normalized mean fluorescence intensity is shown. Tables report the estimated $EC_{50}$ values determined by GraphPad Prism 9 software using non-linear curve fitting (4 parameters). ~ symbol indicates that the reported value is ambiguous due to poor curve fitting.

Figure 6:
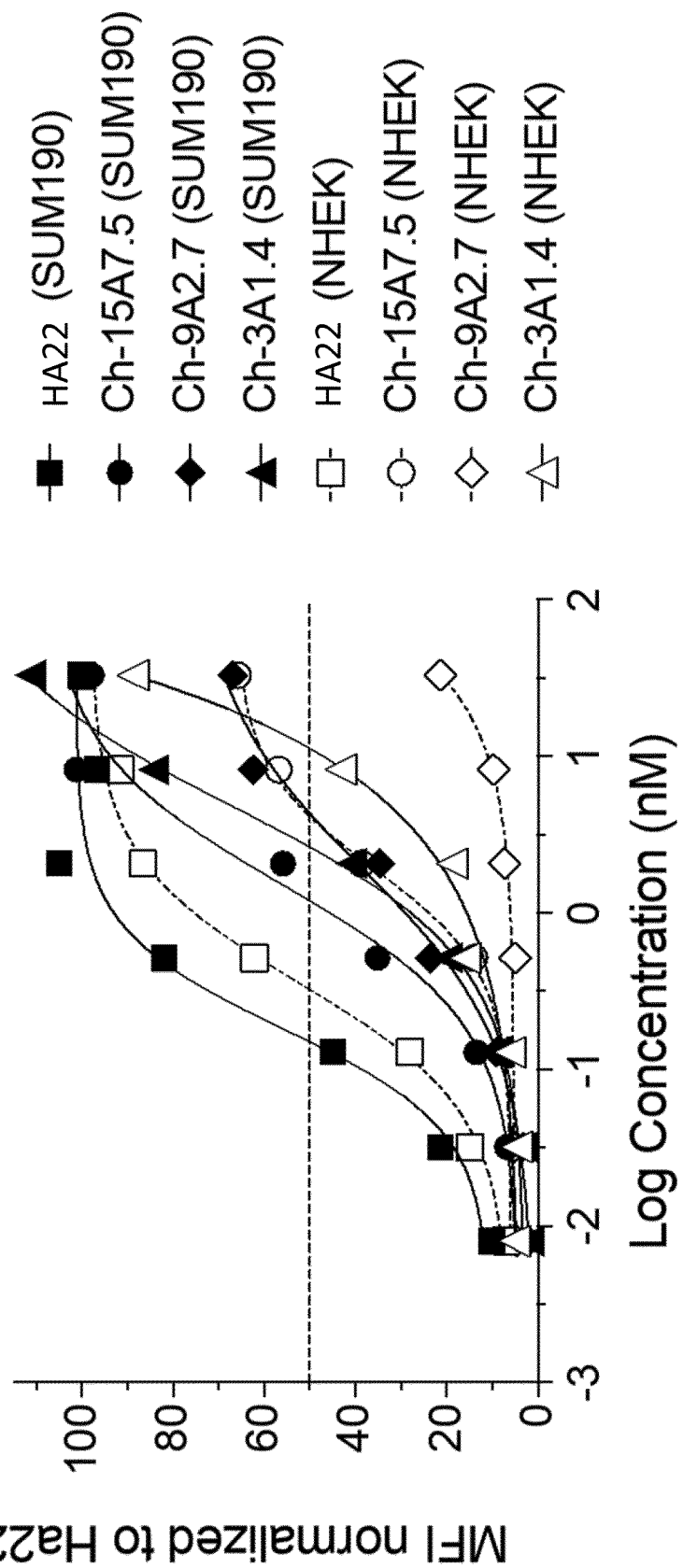

FIG. 6: Differential binding to Nectin-4 expressed by tumor cell line and normal differentiated human keratinocytes. Detection by flow cytometry.

Flow cytometry analysis of TNBC cell line (SUM190, plain symbols) and normal differentiated (0.1 mM $CaCl_2$)) human keratinocytes (NHEK, open symbols) using a dose range (1.2 ng/mL-5 µg/mL)) of Enfortumab (HA22, squares), Ch-15A7.5 (circles), Ch-3A1.4 (triangles) and Ch-9A2.7 (diamonds). Cells were then stained with phycoerythrin conjugate goat anti human Fc antibody. Normalized mean fluorescence intensities are shown. Non-linear curve fitting (4 parameters) was done with GraphPad Prism 9 software. Horizontal bar is placed at 50% of maximum staining intensity obtained with HA22 antibody on SUM190 cells.

FIG. 7: Differential binding to Nectin-4 expressed by tumor cell line and normal differentiated human keratinocytes. Detection by flow cytometry.

Flow cytometry analysis of TNBC cell line (SUM190, A) and normal differentiated (0.1 mM $CaCl_2$)) human keratinocytes (NHEK, B) using 5 µg/mL of HA22 (Enfortumab), Ch-15A7.5, and Ch8F06. Cells were then stained with phycoerythrin conjugate goat anti human Fc antibody. Normalized mean fluorescence intensities are shown.

Figure 8:
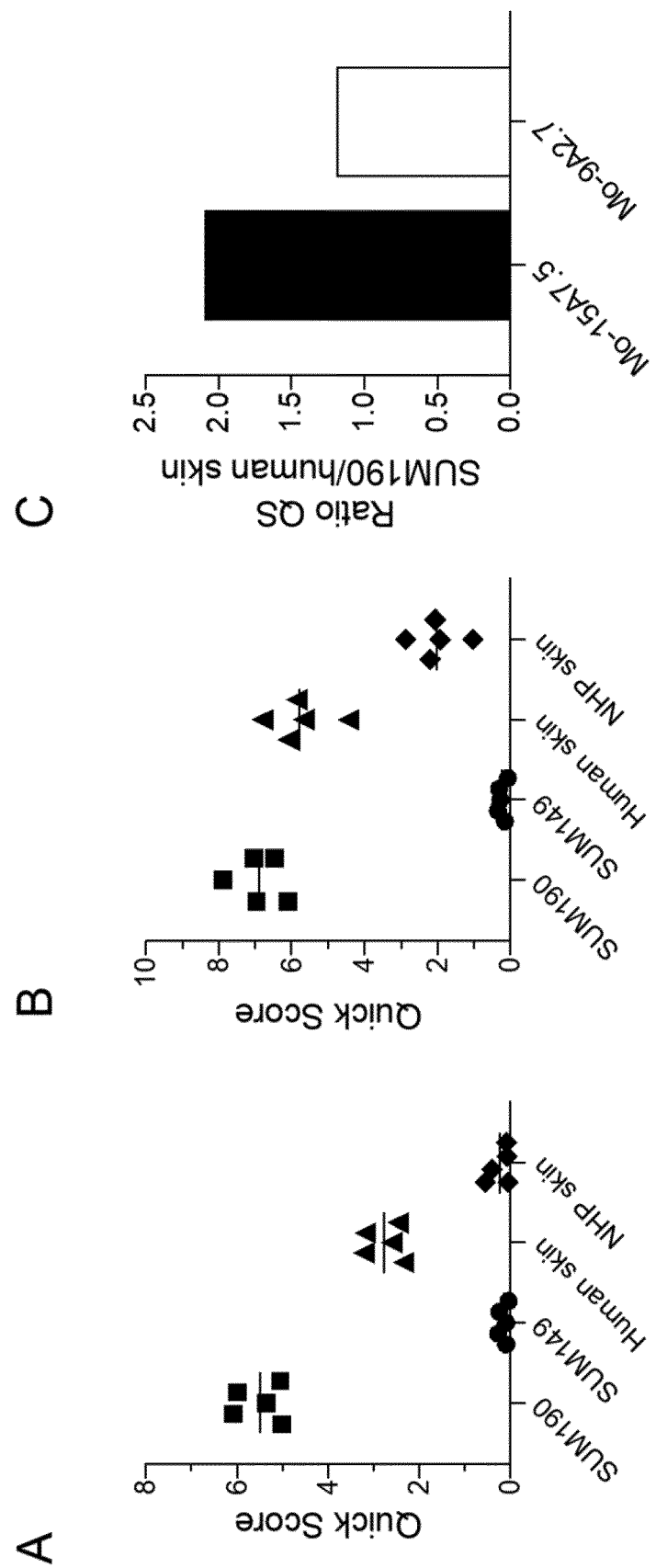

FIG. 8: Differential binding to Nectin-4 expressed by tumor cell line and human keratinocytes. Detection by immuno-histochemistry.

Cryo-preserved OCT-embedded blocks of high expressing levels of Nectin-4 tumor cell line (SUM190), low expressing levels of Nectin-4 tumor cell line (SUM149), human and cynomolgus skin were processed for staining with 15A7.5 mAb (A) and 9A2.7 mAb (B). Quick score reported for each mAb are shown (A, B). C, ratio of quick score SUM190 over human skin.

Figure 9:
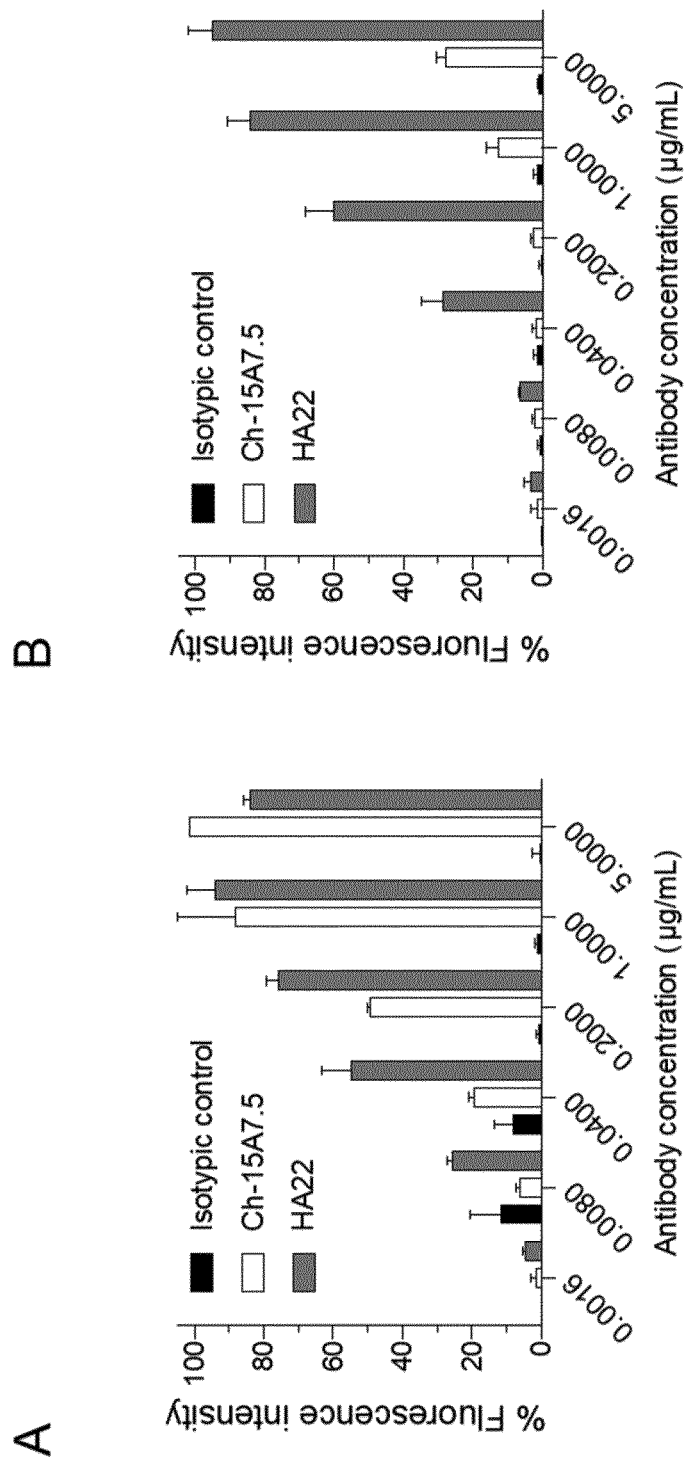

FIG. 9: Differential internalization in tumor cell line and human keratinocytes. Detection by fluorescence Enfortumab (HA22), Ch-15A7.5 and Isotypic control mAbs were coupled to pHAB thiol reactive dye to reach dye antibody ratio comprised between 4.58 and 5.55. A dose range of each of these antibody dye conjugates (1.6 ng/mL-5 µg/m L) was incubated in duplicates with SUM190PT Nectin-4-expressing cell line (A) normal human differentiated (0.1 mM $CaCl_2$)) keratinocytes (B). Intracellular fluorescence was recorded after 24 hours with florescence microplate reader (ClarioStar). Reported are the fluorescence intensities in function of dye antibody conjugate concentration.

Figure 10:
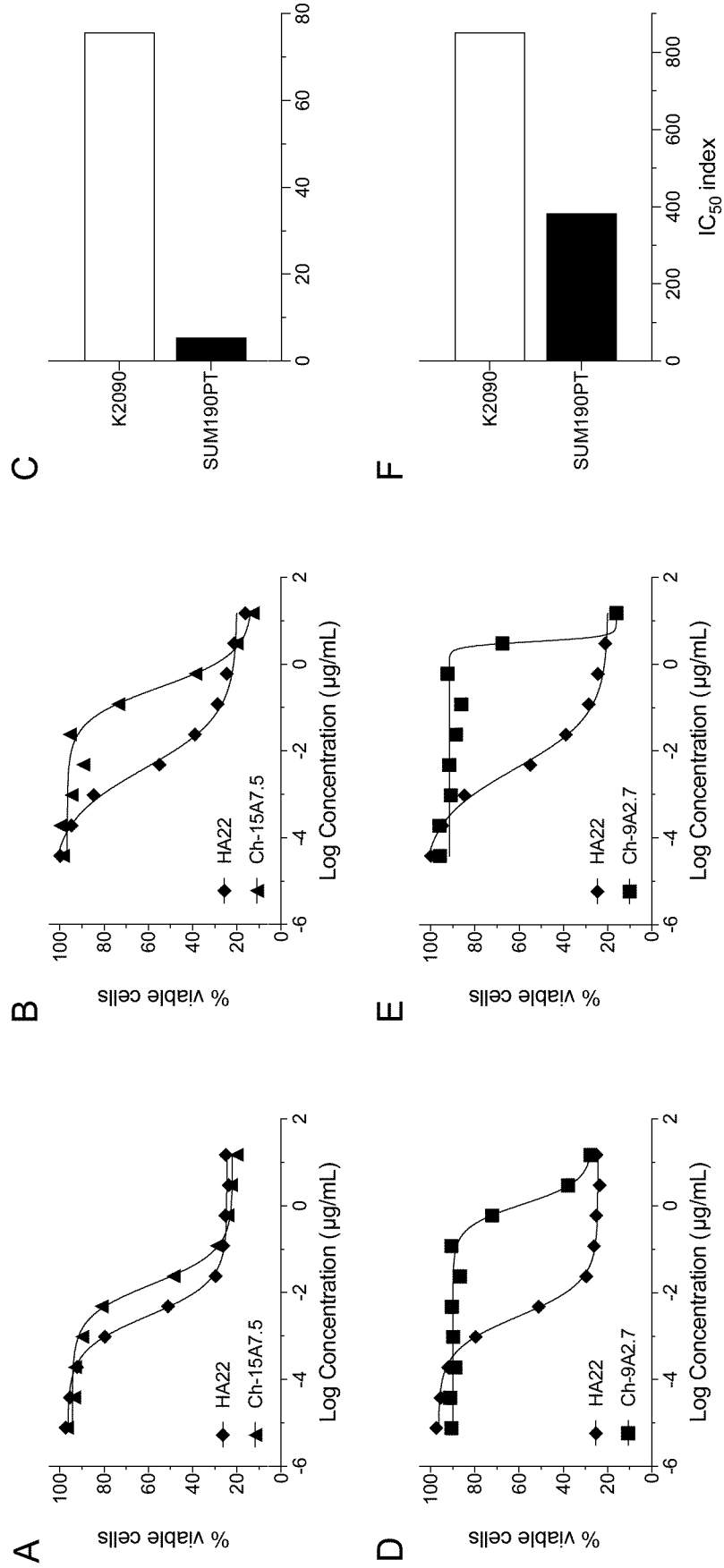

FIG. 10: Differential in vitro cytotoxic activity to tumor cells and normal differentiated human keratinocytes. Cell survival measured by MTT assay.

Enfortumab (HA22, diamonds), Ch-15A7.5 (triangles) and Ch9A2.7 (squares) mAbs were coupled to α-amanitin to generate antibody drug conjugates which cytotoxic activity of a dose range (7.7 pg/mL-15 µg/mL) was comparatively evaluated on SUM190PT Nectin-4-expressing cell line (A, D) or normal human differentiated (0.1 mM $CaCl_2$)) keratinocytes (B, E). Viability (MTT assay) after a 5-days incubation period is reported. $EC_{50}$ values were determined by GraphPad Prism 9 software using non-linear curve fitting (4 parameters). For each condition, the ratio of $EC_{50}$ of Ch-15A7.5 ADC (C) or Ch-9A2.7 ADC (F) to that of HA22-ADC was calculated and reported. Data shown is representative of 2 different Nectin-4 expressing tumor cell lines (SUM190PT and MDA-MB468) and 3 independent donors for human keratinocytes.

Figure 11:
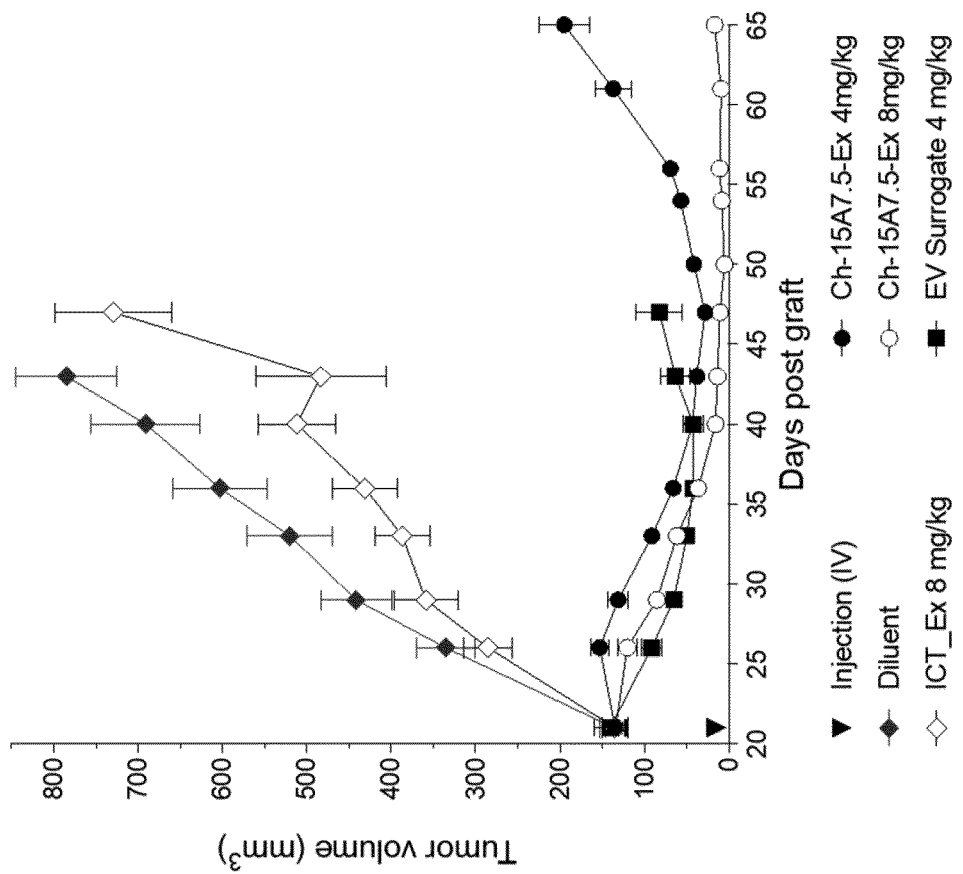

FIG. 11: Treatment of SUM190 grafted NSG mice with Ch-15A7.5-MAPS-ßGlu-Exatecan ADC induces a long-lasting tumor regression period.

NSG mice (n=5/group) were orthotopically xenografted bilaterally with the SUM190PT cells embedded in Matrigel. Three different ADC were tested: Isotypic Control, ICT- and Ch-15A7.5-MA-PS-ßGlu-Exatecan and Enfortumab vedotin surrogate, HA22-MC-vcPABC-MMAE. Treatment of mice (single intravenous injection) started when tumors reached approximately 150 mm³. Ch15A7.5-MA-PS-ßGlu-Exatecan (Ch-15A7.5-Ex) was evaluated at 2 doses (4 or 8 mg/kg), ICT-MA-PS-ßGlu-Exatecan (ICT-Ex) was given at 8 mg/kg and Enfortumab vedotin (EV) surrogate was given at 4 mg/kg. Tumor sizes (n=10/group) were monitored with a caliper twice a week thereafter and sizes were reported with the following formula (LxlxhxPi/6).

Figure 12:
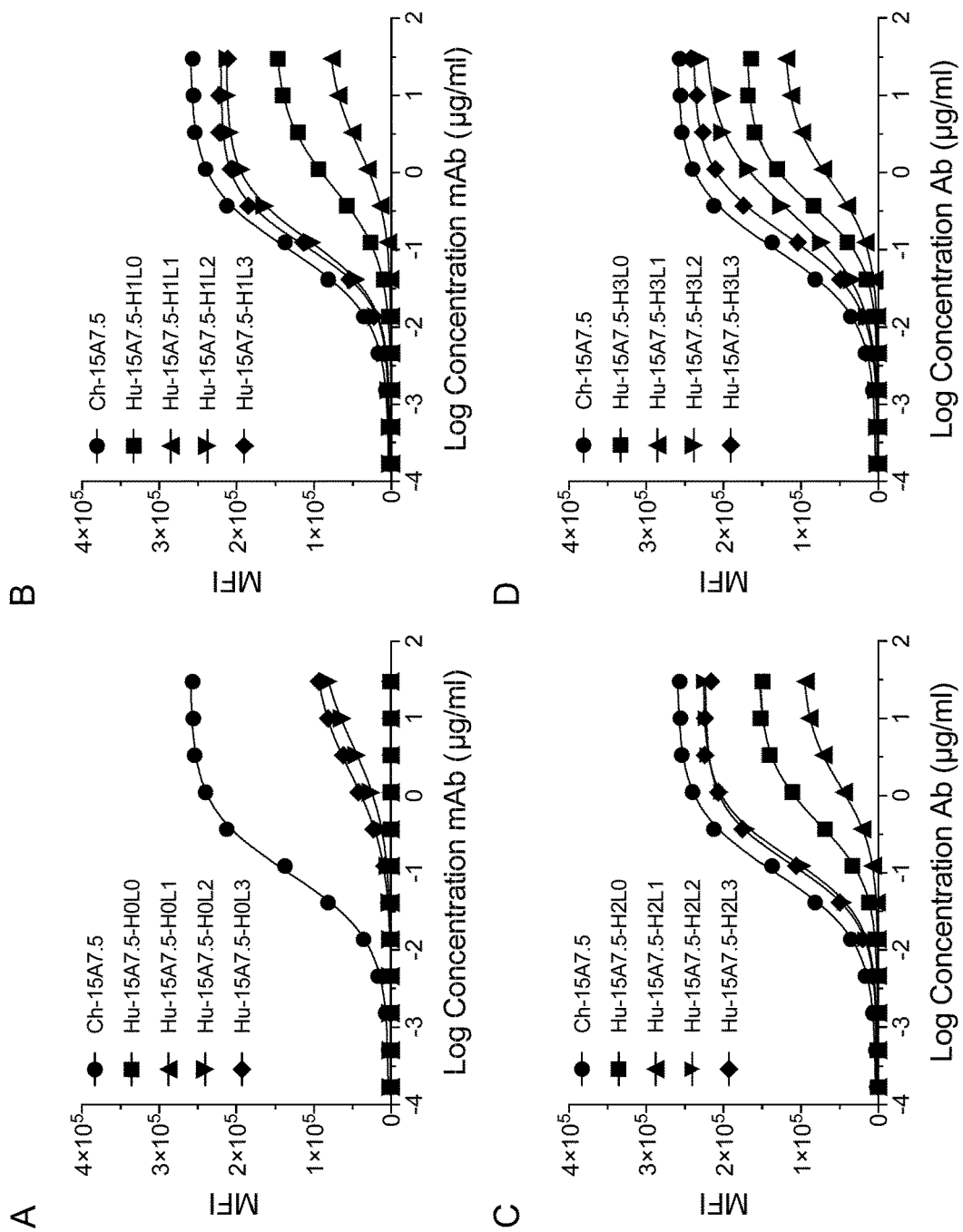

FIG. 12: Apparent affinity of humanized variants to tumor cells. Detection by flow cytometry.

T47D human tumor cells expressing Nectin-4 were numbered and incubated with a dose range (169 pg/mL-30 µg/mL) of Ch15A7.5 or indicated humanized variants. Numbers associated with H and L refer to the number of back mutations introduced. Cells were then stained with phycoerythrin conjugate goat anti human Fc antibody and analyzed by flow cytometry. Mean fluorescence intensities are reported. GraphPad Prism 9 software was used non-linear curve fitting (4 parameters).

Figure 13:
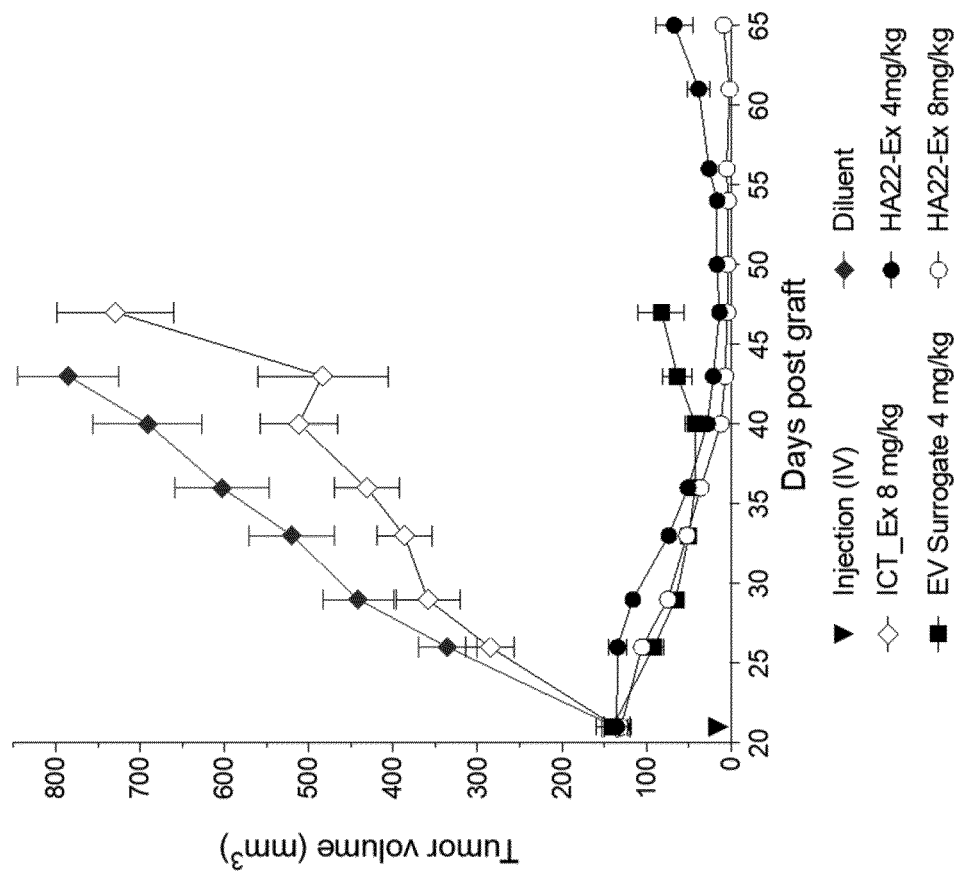

FIG. 13: Treatment of SUM190 grafted NSG mice with HA22-MA-PS-ßGlu-Exatecan ADC induces a long-lasting tumor regression period.

NSG mice (n=5/group) were orthotopically xenografted bilaterally with the SUM190PT cells embedded in Matrigel. Three different ADC were tested: Isotypic Control, ICT- and HA22-MA-PS-ßGlu-Exatecan and Enfortumab vedotin surrogate, HA22-MC-vcPABC-MMAE. Treatment of mice (single intravenous injection) started when tumors reached approximately 150 mm³. HA22MAPS-ßGlu-Exatecan (HA22-Ex) was evaluated at 2 doses (4 or 8 mg/kg), ICT-MA-PS-ßGlu-Exatecan (ICT-Ex) was given at 8 mg/kg and Enfortumab vedotin (EV) surrogate was given at 4 mg/kg. Tumor sizes (n=10/group) were monitored with a caliper twice a week thereafter and sizes were reported with the following formula (LxlxhxPi/6).

Figure 14:
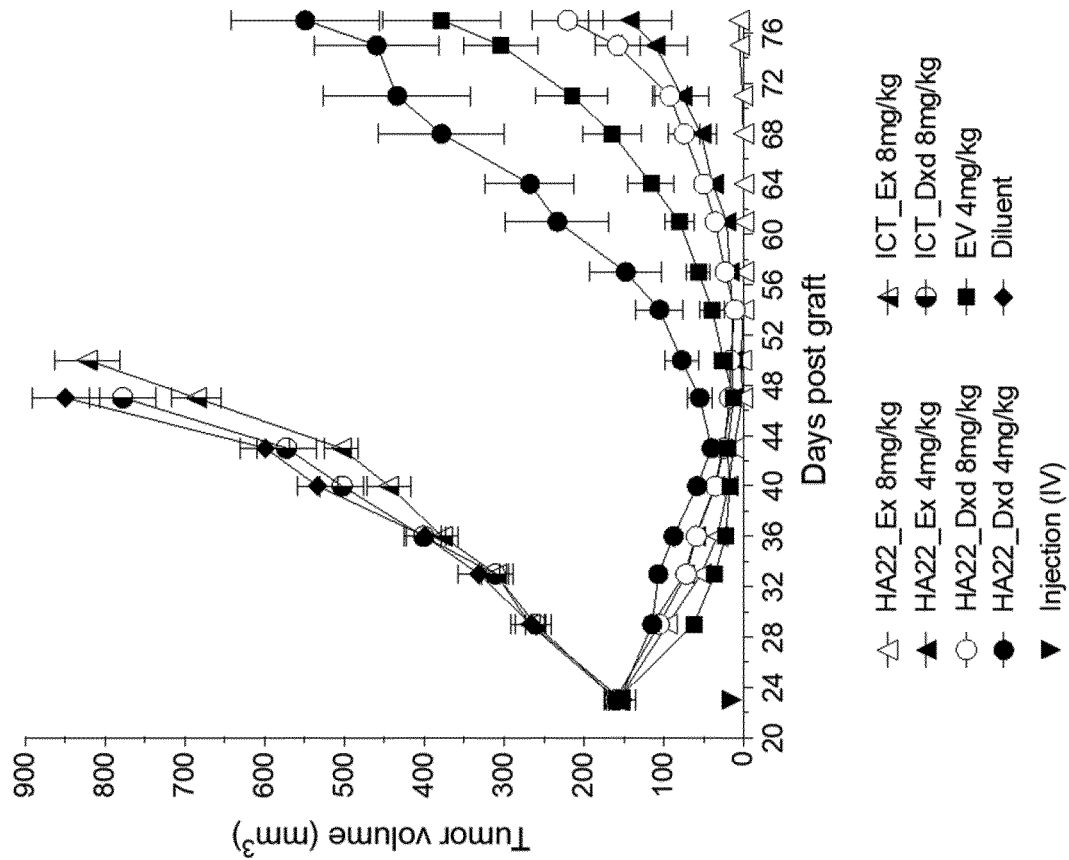

FIG. 14: Treatment of SUM190 grafted NSG mice with HA22-MA-PSßGlu-Exatecan and HA22-MC-GGFG-DX8951 ADC induces a long-lasting tumor regression period.

NSG mice (n=5/group) were orthotopically xenografted bilaterally with the SUM190PT cells embedded in Matrigel. Five different ADC were tested: Isotypic Control, ICT- and HA22 coupled either with MA-PS-ßGlu-Exatecan (ICT-Ex and HA22-Ex) or MCGGFG-DX8951 (ICT- and HA22-Dxd) and Enfortumab vedotin surrogate, HA22-MC-vc-PABC-MMAE (EV). Treatment of mice (single intravenous injection) started when tumors reached approximately 150 mm³. HA22-Ex and HA22-Dxd were evaluated at 2 doses (4 or 8 mg/kg), ICT-EX and ICT-Dxd were given at 8 mg/kg and Enfortumab vedotin (EV) surrogate was given at 4 mg/kg. Tumor sizes (n=10/group) were monitored with a caliper twice a week thereafter and sizes were reported with the following formula (LxlxhxPi/6).

Figure 15:
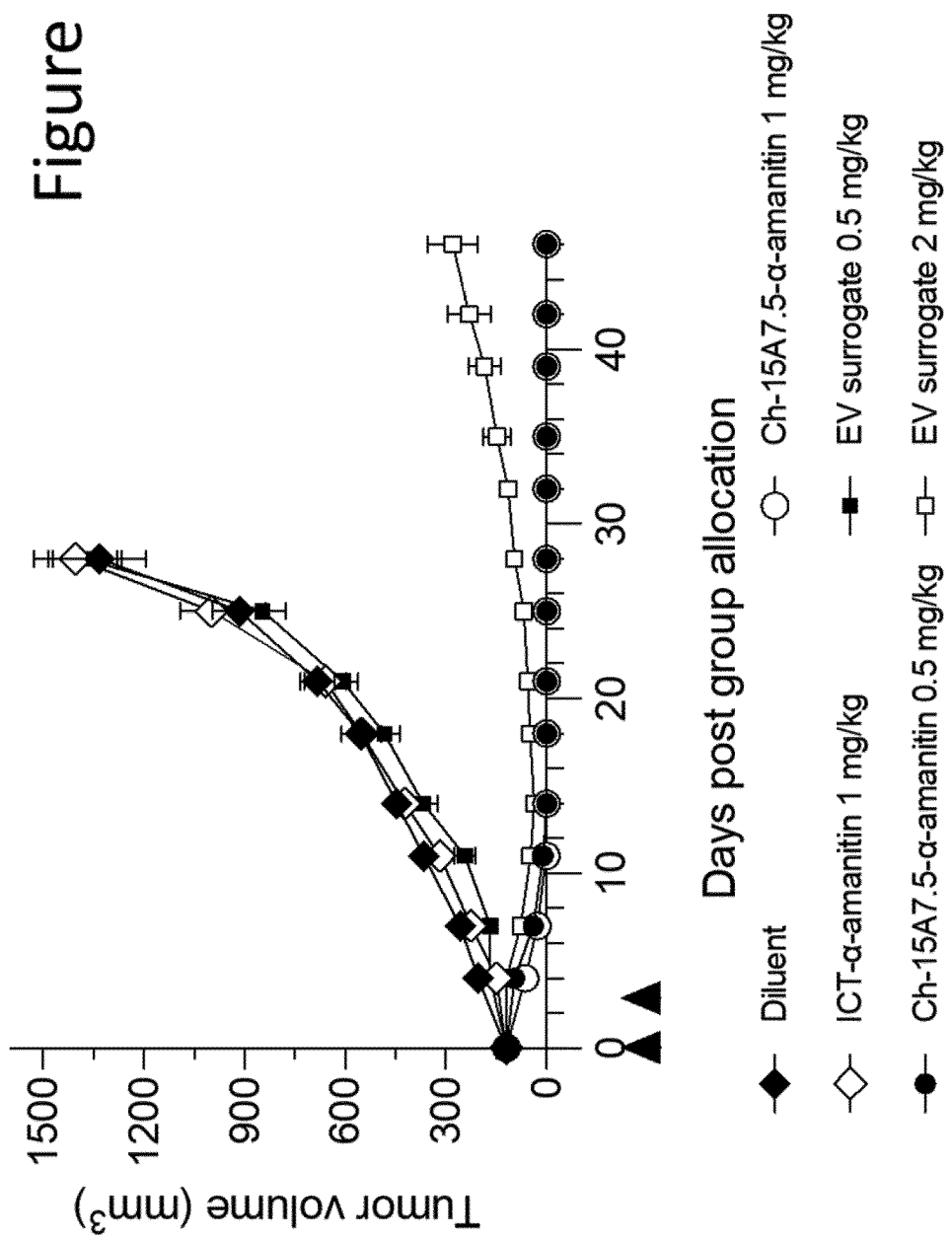

FIG. 15: Treatment of SUM190 grafted NOD-Scid mice with Ch-15A7.5-α-amanitin ADC induces a long-lasting tumor regression period. NOD-Scid mice (n=10/group) were orthotopically xenografted with the SUM190PT cells embedded in Matrigel. Three different ADC were tested: Isotypic Control, ICT- and Ch-15A7.5-α-amanitin and Enfortumab vedotin surrogate, HA22-MC-vc-PABC-MMAE (EV surrogate). Treatment of mice (2 intravenous injections at a 7-days interval, arrow heads) started when tumors reached approximately 120 mm³. Ch-15A7.5-α-amanitin was evaluated at 2 doses (0.5 or 1 mg/kg), ICT-α-amanitin was given at 1 mg/kg and Enfortumab vedotin (EV) surrogate was given at 0.5 or 2 mg/kg. Tumor sizes (n=10/group) were monitored with a caliper twice a week thereafter and sizes were reported with the following formula (LxlxhxPi/6).

Figure 16:
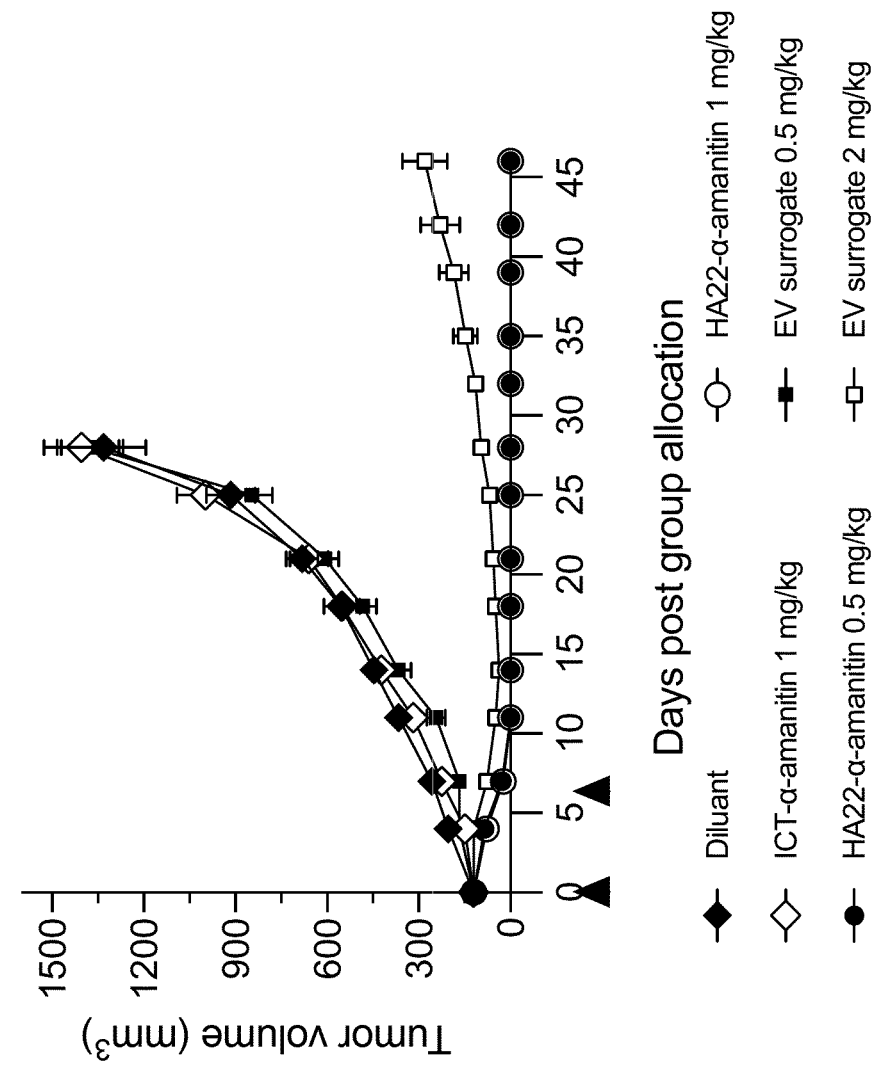

FIG. 16: Treatment of SUM190 grafted NOD-Scid mice with HA22-α-amanitin ADC induces a long-lasting tumor regression period.

NOD-Scid mice (n=10/group) were orthotopically xenografted with the SUM190PT cells embedded in Matrigel. Three different ADC were tested: Isotypic Control, ICT- and HA22-α-amanitin and Enfortumab vedotin surrogate, HA22-MC-vc-PABC-MMAE (EV surrogate). Treatment of mice (2 intravenous injections at a 7-days interval, arrow heads) started when tumors reached approximately 120 mm³. HA22-α-amanitin was evaluated at 2 doses (0.5 or 1 mg/kg), ICT-α-amanitin was given at 1 mg/kg and Enfortumab vedotin (EV) surrogate was given at 0.5 or 2 mg/kg. Tumor sizes (n=10/group) were monitored with a caliper twice a week thereafter and sizes were reported with the following formula (LxlxhxPi/6).

Figure 17:
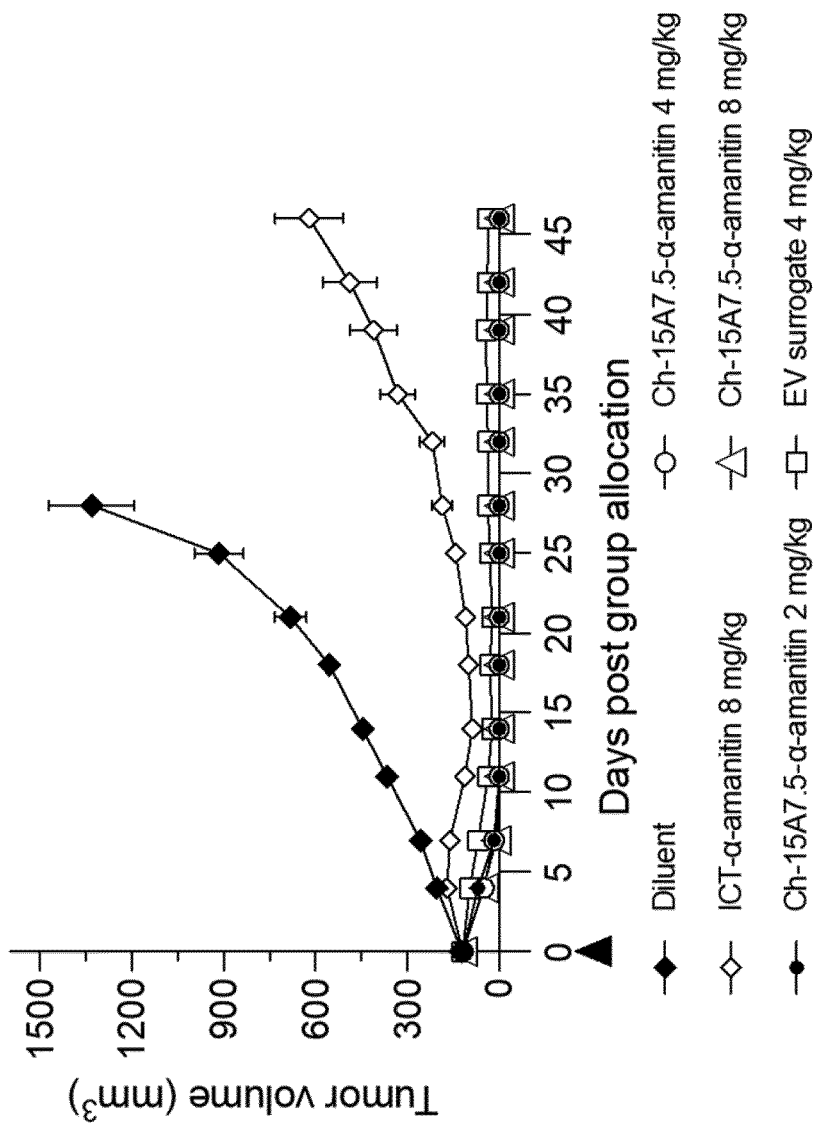

FIG. 17: Treatment of SUM190 grafted NOD-Scid mice with Ch-15A7.5-α-amanitin ADC induces a long-lasting tumor regression period. NOD-Scid mice (n=10/group) were orthotopically xenografted with the SUM190PT cells embedded in Matrigel. Three different ADC were tested: Isotypic Control, ICT- and Ch-15A7.5-α-amanitin and Enfortumab vedotin surrogate, HA22-MC-vc-PABC-MMAE (EV surrogate). Treatment of mice (1 intravenous injection, arrow head) started when tumors reached approximately 120 mm³. Ch-15A7.5-α-amanitin was evaluated at 3 doses (2, 4 and 8 mg/kg), ICT-α-amanitin was given at 8 mg/kg and Enfortumab vedotin (EV) surrogate was given at 4 mg/kg. Tumor sizes (n=10/group) were monitored with a caliper twice a week thereafter and sizes were reported with the following formula (LxlxhxPi/6).

Figure 18:
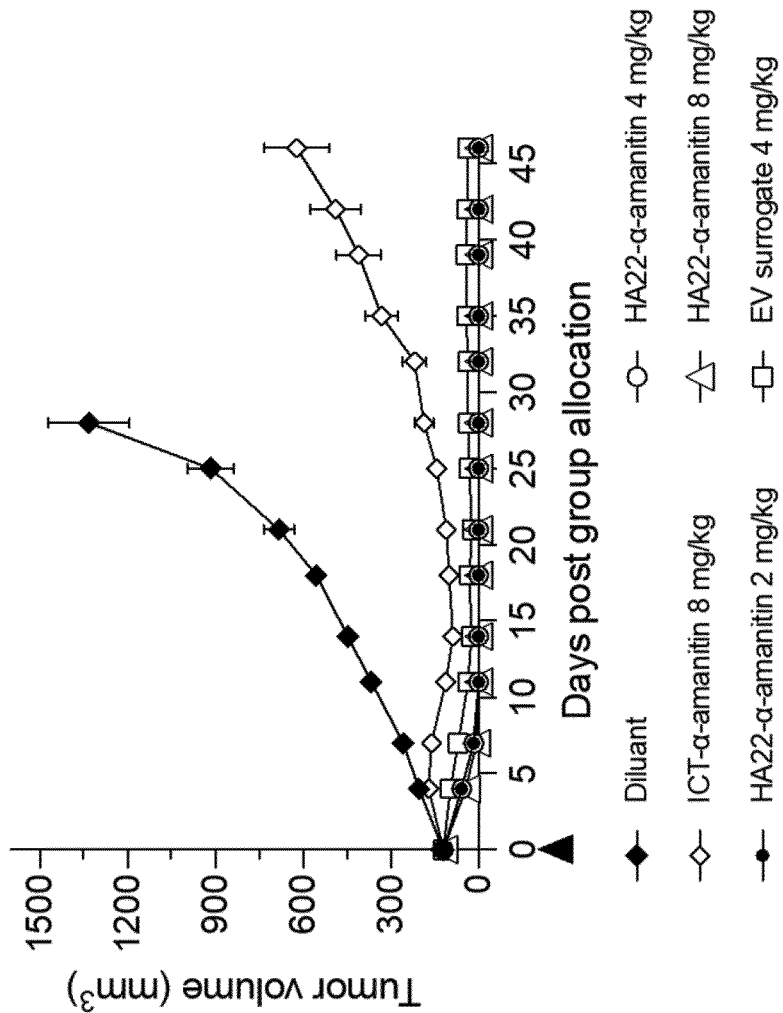

FIG. 18: Treatment of SUM190 grafted NOD-Scid mice with HA22-α-amanitin ADC induces a long-lasting tumor regression period.

NOD-Scid mice (n=10/group) were orthotopically xenografted with the SUM190PT cells embedded in Matrigel. Three different ADC were tested: Isotypic Control, ICT- and HA22-α-amanitin and Enfortumab vedotin surrogate, HA22-MC-vc-PABC-MMAE (EV surrogate). Treatment of mice (1 intravenous injection, arrow head) started when tumors reached approximately 120 mm³. HA22-α-amanitin was evaluated at 3 doses (2, 4 and 8 mg/kg), ICT-α-amanitin was given at 8 mg/kg and Enfortumab vedotin (EV) surrogate was given at 4 mg/kg. Tumor sizes (n=10/group) were monitored with a caliper twice a week thereafter and sizes were reported with the following formula (LxlxhxPi/6).

Figure 19:
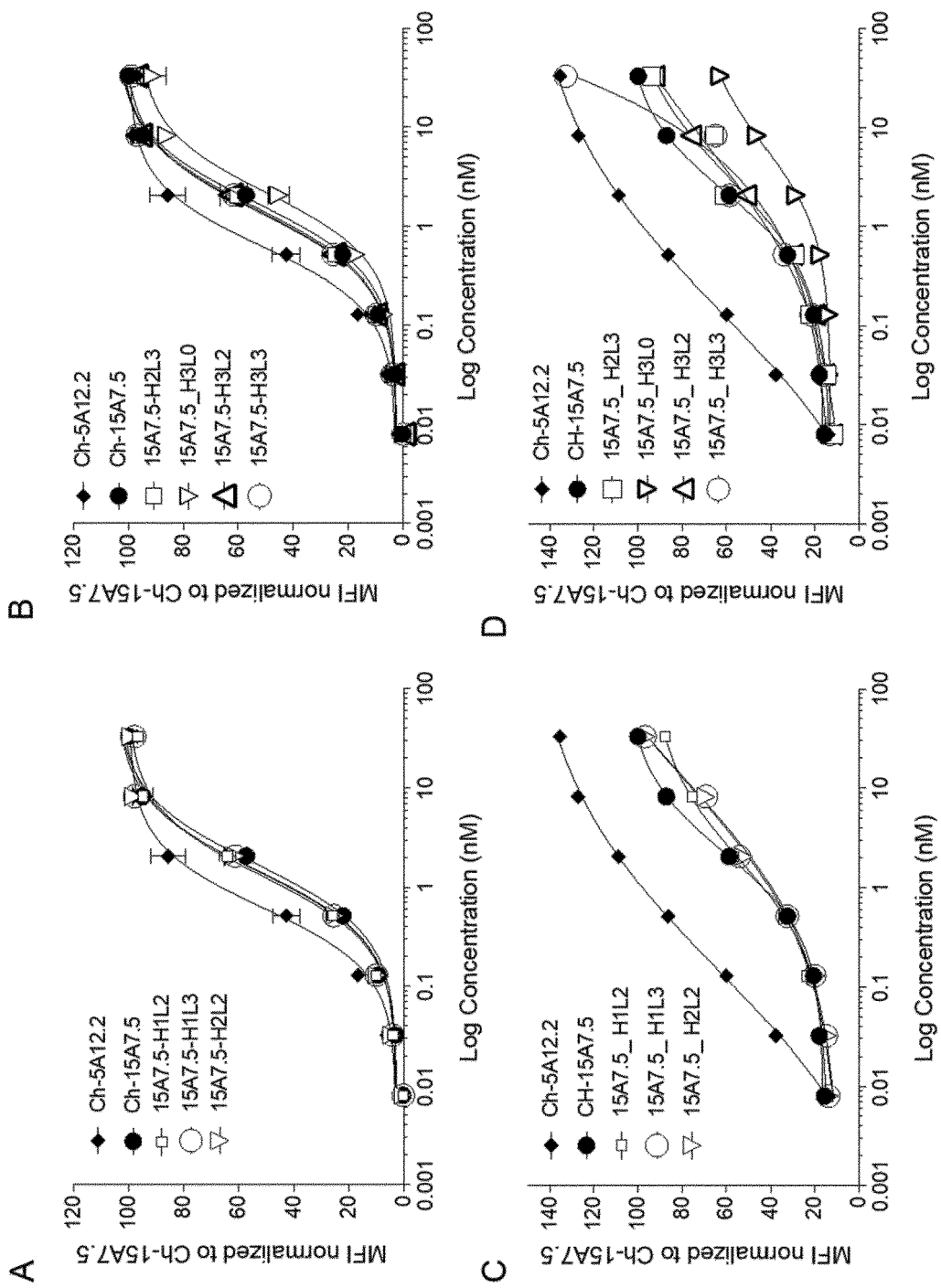

FIG. 19: Differential binding of Ch-15A7.5 and its humanized variants to Nectin-4 expressed by tumor cell line and normal differentiated human keratinocytes. Detection by flow cytometry.

Flow cytometry analysis of TNBC cell line (SUM190, upper panels) and normal differentiated (0.1 mM $CaCl_2$)) human keratinocytes (NHEK, lower panels) using a dose range (8 pM-33 nM) of Ch-5A12.2, Ch-15A7.5 and its humanized variants 15A7.5-H1L2, -H1L3, -H2L2, -H2L3, -H3L0, -H3L2, -H3L3. Cells were then stained with phycoerythrin conjugate goat anti human Fc antibody. Normalized mean fluorescence intensities are shown. Non-linear curve fitting (4 parameters) was done with GraphPad Prism 9 software. Note the much lower apparent $EC_{50}$ of Ch and its humanized variants towards keratinocytes (lower panels) in comparison to that of Ch-5A12.2.

FIG. 20: Amino acid sequence of the variable heavy chain (VH) and variable light chain (VK) of the parental antibody clone 5A12.2. The H-CDR and L-CDR sequences according to the IMTG nomenclature are underlined.

FIG. 21: Amino acid sequences of the variable heavy chains (VH) and variable light chains (VK) of humanized variants of 9A2.7. The H-CDR and L-CDR sequences according to the IMTG nomenclature are underlined FIG. 22: Amino acid sequences of the variable heavy chains (VH) and variable light chains (VK) of humanized variants of 3A1.4. The H-CDR and L-CDR sequences according to the IMTG nomenclature are underlined.

FIG. 23: Amino acid sequences of the variable heavy chains (VH) and variable light chains (VK) of humanized variants of 8F06. The H-CDR and L-CDR sequences according to the IMTG nomenclature are underlined FIG. 24: Amino acid sequences of the variable heavy chains (VH) and variable light chains (VK) of parental antibody clone 15A7.5. The H-CDR and L-CDR sequences according to the IMTG nomenclature are gray-shaded.

FIG. 25: Amino acid sequences of the variable heavy chains (VH) and variable light chains (VL) of humanized variants of 15A7.5. The H-CDR and L-CDR sequences according to the IMTG nomenclature are gray-shaded.

FIG. 26: Affinity values of humanized 15A7.5 variants

EXAMPLES

Materials and Methods
Cell Lines:

Human breast carcinoma cell line MDA-MB231 (ATCC, Manassas, VA) was cultured in DMEM supplemented with 10% fetal bovine serum, 50 IU/mL penicillin, 50 µg/mL streptomycin and 2 mM glutamine. The cells were transfected with expression vector p3XFLR4.C1 containing a PVRL4 cDNA. Human triple negative breast cancer cell line SUM190PT (BiolVT, Westbury, NY) was cultures in Ham's F12 medium with 5% fetal bovine serum, 1% non-essential amino acids, 1% Hepes, 1% insulin, 1 µg/mL hydrocortisone, 6.8 ng/mL Triiodo L-tyrosine, 100 IU/mL penicillin, 100 µg/mL streptomycin and 2 mM glutamine. Chinese hamster ovary CHO cell line was cultured in DMEM supplemented with 10% fetal bovine serum, 100 IU/mL penicillin, 100 µg/mL streptomycin and 2 mM glutamine. Human breast carcinoma MDA-MB-468 cell line and T47D cell line were cultured in RPMI supplemented with 10% fetal bovine serum, 100 IU/mL penicillin, 100 µg/mL streptomycin.

ELISA:

A sandwich enzyme-linked immunosorbent assay was used to control specificity of Ch-15A7.5 antibody and to perform competition assays between different mabs. Ninety-six-wells plates were coated with 10 nM of Nectin-4-VCC-Fc, Nectin-1-VCC-Fc (entire extracellular part) or Nectin-4-V-Fc (comprising only the IgV domain) overnight at +4° C. After washes and saturation with PBS 1% BSA, cells were incubated for 2 hours at 25° C. with 10 nM of peroxidase-conjugated Ch-15A7.5 mab. In the case of competition, binding of 0.5 nM of peroxidase conjugated Ch-15A7.5 mab was measured in the presence of variable concentration (0.018 nM to 40 nM) of "cold" mab. One hundred µL of peroxidase substrate was added (One Step ABST, Pierce), and OD was red at 405 nm.

Flow Cytometry:

Cells or cell lines (10,000-50,000) expressing Nectin-4 (naturally or transfected) were incubated with dose range of the indicated antibodies. After washing, cells were then stained with phycoerythrine-conjugated goat anti human antibody (5 µg/mL) Jackson Immuno Research). After fixation, cells were stained with a viability dye (e780, Invitrogen) before flow cytometry acquisition.

Immunohistochemistry:

Frozen samples stored at −80° C. were kept on dry ice and placed in plastic cryomolds in a way that would allow to maximize the number of subsequent sections and were embedded in Optimal Cutting Temperature (OCT) medium. Frozen blocks of OCT were mounted on disks with OCT and cryosection were performed at −20° C. on a NX70 cryostat (Thermo Scientific). Cryosections (7 µm) were mounted on superfrost+slides (VWR). Only the requested number of slides for each sery of test were prepared and stored at −80° C. until use. Remaining blocks were stored at −80° C. until further use. Sections were arranged on the slide and fixed in Acetone at −20° C. for 10 minutes. Endogenous peroxidases were inhibited by immersing the slides in hydrogen peroxide ($H_2O_2$) as part of Roche DAB kit protocol. Several dilution of each mab were tested to optimize noise to signal ratio and 0.5 µg/mL of mouse 15A7.5 mab and 10 µg/mL of mouse 9A2.7 mab were determined as optimal. In order to mitigate the non specific binding of the secondary antibody to the mouse tissue, a Rabbit anti-mouse IgG (4 µg/mL, Abcam) was added following primary Ab incubation. The omni-map anti-rabbit HRP (Roche) was then used to perform the DAB staining according to manufacturer's instruction (Ventana automat). An assessment of both the staining intensity and the proportion of stained cells was performed. Two trained technicians observed the same microscope field independently and sequentially. Both the stained cells proportion and the staining intensity were evaluated for each field. For each staining, 10 fields were chosen randomly at the magnification which allowed the best visualization of tissues. Scoring procedure was as follows: (i) The proportion of cells stained positively was estimated and a score from 0 to 4 was be assigned for each field (0=0-5%; 1=5-25%; 2=25-50%; 3=50-75%; and 4=75-100%); and (ii) The staining intensity was scored as 0, 1, 2, or 3 corresponding to the presence of negative, weak, intermediate, and strong brown staining, respectively. The final Score for each field and for each observer was the multiplication of the two values (0=No staining in the tissue; 12=tissue contains strongly stained cells). For each tissue type, on each of the 5 slides of each set of slides, 10 independent observation fields were scored in parallel for both staining intensity and percentage of labeled cells. Technicians simultaneously observed a given field (virtual slide, on computer screen) and independently scored, blind of the other observer results. For each slide, the 10 scores of each technician were averaged to set the final score for each observer. Final scores of the two observers were averaged yielding the tissue score for the given slide. For the human skin, only results from the first set of the repeatability are presented.

Internalization Assay

Ten thousand SUM190PT or human differentiated keratinocytes (0.1 mM $CaCl_2$)) were seeded in 96-wells plates and subsequently incubated for 24 hours at 37° C., with a dose range (1.6 ng/mL-5 µg/mL) of anti Nectin-4 mAbs and isotypic control conjugated with pHAB thiol reactive dye. Upon internalization and endo-lysosomal processing, the acidic environment causes the dye to fluoresce. Fluorescence intensity was monitored on a plate reader with an excitation at 532 nm and an emission at 560 nm.

In Vitro Cytotoxic Assay

To analyze the in vitro cytotoxic activity of ADC, cell viability was assessed using the AlamarBlue staining protocol as recommended by the manufacturer (Biosource, CA, USA). The test incorporates a fluorescent oxidation-reduction indicator. Fluorescence intensity is proportional to cellular metabolic reduction. Experiments were done by incubating 3000 cells/well (SUM190PT or differentiated NHEK) in triplicate with serial dilutions of ADC at Day 0 in 96-wells plates. AlamarBlue was measured at Day 5 by incubating 1/10 volume of alamarBlue solution for 2 h at 37° C. and read at 595 nm (FLUOstar Optima, BMG Labtech).

Mouse Experiments

NOD/SCID (nonobese diabetic/severe combined immunodeficient)/gc null mice (NSG) were obtained from Charles River Laboratory (Margate, UK). Six to seven-weeks old females (n=5/group) were orthotopically xenografted bilaterally with the SUM190PT (0.5×10 6) cells embedded in Matrigel. Treatment with ADC was performed as mentioned in the respective experiments. Tumor sizes (n=10/group) were monitored with a caliper twice a week thereafter and sizes were reported with the following formula (LxlxhxPi/6)

Hybridoma Sequencing

For hybridoma sequencing, RNA was first extracted from hybridoma cell pellets. cDNA was generated by reverse transcription and VH and VL domains were amplified by polymerase chain reaction using Prime STARMax DNA Polymerase (Takara). PCR products were subsequently cloned into dedicated heavy and light chain expression vector and then sequenced.

Chimeric Antibodies Generation, Production, Purification and Control

Light chain expression vector is coding for a V kappa chain. Depending on the payload used, 2 different heavy chain expression vectors were used, one coding for a Fc fragment with D265C (ThiomAb) L234A and L235A mutations, one coding for a Fc fragment with P331S, L234Q and L235F mutations. Both Fc fragments are "Fc-silent". The sequences of anti-Nectin-4 Enfortumab (HA22) were also cloned in the same vectors.

Light and heavy chain vectors were transfected in HEK293 seeded with a 1.2/1 ratio. After 6 days of production, culture supernatants were clarified and mAbs were purified using MabSelect PrismA resin (GE Healthcare) according to the manufacturer's instructions. 0.5M Glycine, 3M NaCl, pH8.9 was used as binding buffer, and 0.1 M Citrate pH 3 was used for elution. Instant neutralization was done with 10% (V/V) 1M Tris-HCl pH 9. Monoclonal chimeric antibodies were then dialyzed against PBS 1×pH 7.4 (Mini dialysis devices, 2 mL-10k, Thermo Scientific) followed by filtration on 0.22 µM filter (Milelex GV hydrophilic PVDF, Millipore). Concentration was determined with a Nanodrop 2000 Spectrophotometer (Thermo Scientific) taking into account the specific extinction coefficient ($E^{1\%}{}_{280nm}$) of each monoclonal antibody. Purity was determined by UPLC-SEC using an Acquity UPLC-HClass Bio (Waters) using a ProteinBEH 200A column equilibrated in 0.2 M $NaPO_4$, 0.3 M NaCl pH 6.9 supplemented with 10% isopropanol. The mass of the antibodies was determined in a Xevo G2-S Q-Tof mass spectrophoyometer (Waters) using a reversed-phase column (PLRP-S 4000A, Agilent technologies). All samples were analyzed after deglycosylation with PNGase F glycosidase (New England Biolabs) at 37° C., according to the manufacturer's instructions. Fragmentation and/or aggregation of the final material was evaluated by SDS-PAGE. Endotoxin load was determined using a chromogenic LAL-kinetic assay (Charles River Endosafe).

Antibody Conjugation

The thiol reactive dye pHAB (Promega) was conjugated to cysteine of selected anti-Nectin-4 ThiomAb (D265C, L234A, L235A) antibodies using maleimide chemistry according to manufacturer's instructions. Briefly, antibodies were dialyzed against 0.1 M Phosphate buffer pH 7.0 before being reduced with 2.5 mM for 1 h at room temperature under mild agitation. Subsequently, DTT was removed by washing/centrifugation twice on Zeba spin desalting columns (7 MWCO). 1.2 L of pH dye reagent (10 µg/mL DMSO) was added to 100 µg of antibody and incubated 1 hour at room temperature protected form light. After removal of excess dye with Zeba desalting columns, Dye antibody ratio were calculated to verify equivalent conjugation between different antibodies.

A cysteine reactive linker-amanitin compound (Heidelberg Pharma) with a cleavable linker (valine alanine) or with a non-cleavable linker was conjugated to engineered cysteine residues of selected anti-Nectin-4 ThiomAb (D265C, L234A, L235A) antibodies using maleimide chemistry. Briefly, ThiomAb antibodies in PBS 1×pH 7.4 were reduced with TCEP and interchains disulfides were re-oxidized by dehydroascorbic acid. Subsequently, the engineered cysteines were used for conjugation with cysteine reactive linker amanitin compound HDP 30.1699. The conjugates were purified by dialysis. The drug-antibody ratio (DAR) according to LC-MS analysis was comprised between 1.44 and 1.79 toxins per conjugated mAb. As determined by SEC-HPLC, less than 2% material was aggregated.

The cysteine reactive linker-exatecan compound Maleimide-Gly-PSAR10-glucuronide-exatecan (MabLink) was conjugated to cysteine residues of selected anti-Nectin-4 mAbs (P331S, L234Q and L235F). In brief, mAbs in PBS 1×, 1 mM EDTA were reduced with 14 molar equivalent of TCEP for 2 hours at 37° C., after which the buffer was exchanged (Amicon ultra 30 kDa) to 100 mM $KPO_4$, 1 mM EDTA pH 7.4. Twelve molar equivalents of the cysteine reactive linker-exatecan compound were used for conjugation with reactive cysteines for 35 min at room temperature. Buffer was then exchanged to 100 mM $KPO_4$ pH 8.0, before incubation at 37° C. for 24 hours in absence of oxygen to allow the maleimide to self-hydrolyze. The final exchange buffer was performed in 20 mM His pH 6.0 before filtration 0.22 µM filter. The drug-antibody ratio (DAR) according to LC-MS analysis was comprised between 7.77 and 7.82 toxins per conjugated mAb. As determined by SEC-HPLC, less than 8% material was aggregated.

The invention claimed is:

1. A monoclonal antibody or antigen-binding fragment thereof which binds to Nectin-4 comprising
   (a) a variable heavy chain (VH) region comprising complementarity-determining regions (CDRs) CDR-H1, CDR-H2 and CDR-H3, wherein
      (i) the CDR-H1 comprises an amino acid sequence according to SEQ ID NO: 7,
      (ii) the CDR-H2 comprises an amino acid sequence according to SEQ ID NO: 8,
      (iii) the CDR-H3 comprises an amino acid sequence according to SEQ ID NO: 9,
      and
   (b) a variable light chain (VL) region comprising complementarity-determining regions (CDRs) CDR-L1, CDR-L2 and CDR-L3, wherein
      (i) the CDR-L1 comprises an amino acid sequence according to SEQ ID NO: 10,
      (ii) the CDR-L2 comprises an amino acid sequence according to SEQ ID NO: 11,
      (iii) the CDR-L3 comprises an amino acid sequence according to SEQ ID NO: 12.

2. The antibody or antigen-binding fragment of claim 1 comprising
   (a) a VH region comprising an amino acid sequence according to SEQ ID NO: 13 or an amino acid sequence having an identity thereof of at least 85%, at least 90%, at least 95% or at least 99%, and (b) a VL region, particularly a VL region comprising an amino acid sequence according to SEQ ID NO:14 or an amino sequence having an identity thereof of at least 85%, at least 90%, at least 95% or at least 99%.

3. The antibody or antigen-binding fragment of claim 1, which is a chimeric antibody, a multispecific antibody, a bispecific antibody, a human antibody, a humanized antibody or an antigen-binding fragment thereof.

4. The antibody or antigen-binding fragment of claim 1, which is an antibody of class IgG, of class IgM, of class IgA or an antigen-binding fragment thereof, or which is a single-chain antibody, or an antibody Fv fragment.

5. A human or humanized monoclonal antibody or antigen-binding fragment thereof which binds to Nectin-4 comprising
(a) (i) a VH region comprising an amino acid sequence according to SEQ ID NO: 27,
and
(ii) a VL region comprising an amino acid sequence according to SEQ ID NO: 28, or
(b) (i) a VH region comprising an amino acid sequence according to SEQ ID NO: 41,
and
(ii) a VL region comprising an amino acid sequence according to SEQ ID NO: 42, or
(c) (i) a VH region comprising an amino acid sequence according to SEQ ID NO: 55,
and
(ii) a VL region comprising an amino acid sequence according to SEQ ID NO: 56, or
(d) (i) a VH region comprising an amino acid sequence according to SEQ ID NO: 69,
and
(ii) a VL region comprising an amino acid sequence according to SEQ ID NO: 70 or 103, or
(e) (i) a VH region comprising an amino acid sequence according to SEQ ID NO: 41,
and
(ii) a VL region comprising an amino acid sequence according to SEQ ID NO: 56, or
(f) (i) a VH region comprising an amino acid sequence according to SEQ ID NO: 41,
and
(ii) a VL region comprising an amino acid sequence according to SEQ ID NO: 70 or 103, or
(g) (i) a VH region comprising an amino acid sequence according to SEQ ID NO: 55,
and
(ii) a VL region comprising an amino acid sequence according to SEQ ID NO: 70 or 103, or
(h) (i) a VH region comprising an amino acid sequence according to SEQ ID NO: 69,
and
(ii) a VL region comprising an amino acid sequence according to SEQ ID NO: 56.

6. The antibody or fragment of claim 1 in combination with a carrier or excipient suitable for use in medicine.

7. The antibody or fragment of claim 1 in combination with a carrier suitable for administration to a subject suffering from or likely to suffer from cancer associated with Nectin-4 overexpression.

8. A nucleic acid coding for one or more antibodies according to claim 1, or for at least one VL and/or one VH of said antibodies.

9. A vector comprising the nucleic acid according to claim 8.

10. A host cell comprising the vector of claim 9.

11. A pharmaceutical composition comprising an antibody or antigen-binding fragment thereof according to claim 1.

12. The antibody or antigen-binding fragment of claim 4, wherein said antibody of class IgG, has a subclass selected from the group consisting of IgG1, IgG2, IgG3 and IgG4.

13. The antibody or fragment of claim 6, wherein said carrier or excipient is suitable for therapeutic or diagnostic applications.

14. The antibody or fragment of claim 13, wherein said diagnostic applications include in vitro and in vivo diagnostic applications.

15. The antibody or antigen-binding fragment of claim 1, wherein said antibody is a chimeric antibody or an antigen-binding fragment thereof.

16. The antibody or antigen-binding fragment of claim 1, wherein said antibody is a humanized antibody or an antigen-binding fragment thereof.

17. The antibody or antigen-binding fragment of claim 1, wherein said antibody is an antibody of subclass IgG1 or an antigen-binding fragment thereof.

18. The antibody or antigen-binding fragment of claim 1, wherein said antibody is an antibody of subclass IgG2 or an antigen-binding fragment thereof.

19. The antibody or antigen-binding fragment of claim 1, wherein said antibody is an antibody of subclass IgG3 or an antigen-binding fragment thereof.

20. The antibody or antigen-binding fragment of claim 1, wherein said antibody is an antibody of subclass IgG4 or an antigen-binding fragment thereof.

* * * * *